United States Patent
Hongo et al.

(10) Patent No.: US 10,321,928 B2
(45) Date of Patent: Jun. 18, 2019

(54) INFORMATION PROCESSING DEVICE, INFORMATION PROCESSING METHOD, AND PROGRAM

(71) Applicant: SONY CORPORATION, Tokyo (JP)

(72) Inventors: Kazuo Hongo, Kanagawa (JP); Kenichiro Nagasaka, Tokyo (JP); Naoki Komine, Saitama (JP); Hiroyuki Suzuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 117 days.

(21) Appl. No.: 15/512,620

(22) PCT Filed: Sep. 8, 2015

(86) PCT No.: PCT/JP2015/075489
§ 371 (c)(1),
(2) Date: Mar. 20, 2017

(87) PCT Pub. No.: WO2016/056339
PCT Pub. Date: Apr. 14, 2016

(65) Prior Publication Data
US 2017/0290601 A1    Oct. 12, 2017

(30) Foreign Application Priority Data

Oct. 9, 2014  (JP) ................. 2014-207980

(51) Int. Cl.
*G06F 19/00* (2018.01)
*A61B 17/29* (2006.01)
(Continued)

(52) U.S. Cl.
CPC .............. *A61B 17/29* (2013.01); *A61B 34/37* (2016.02); *A61B 34/76* (2016.02); *B25J 3/00* (2013.01);
(Continued)

(58) Field of Classification Search
CPC ......... A61B 17/29; A61B 34/37; A61B 34/76; A61B 2090/064; A61B 2090/065;
(Continued)

(56) References Cited

U.S. PATENT DOCUMENTS

2010/0204713 A1* 8/2010 Ruiz Morales .......... B25J 9/041
606/130
2012/0078053 A1* 3/2012 Phee .................. A61B 1/00147
600/139

(Continued)

FOREIGN PATENT DOCUMENTS

CN      104363852 A    2/2015
EP        2861178 A1    4/2015
(Continued)

OTHER PUBLICATIONS

International Search Report and Written Opinion of PCT Application No. PCT/JP2015/075489, dated Nov. 10, 2015, 09 pages of English Translation and 08 pages f ISRWO.
(Continued)

*Primary Examiner* — Ronnie M Mancho
(74) *Attorney, Agent, or Firm* — Oblon, McClelland, Maier & Neustadt, L.L.P.

(57) ABSTRACT

[Object] To enable to detect a force acting on a surgical instrument with a simpler configuration.
[Solution] Provided is an information processing device including an acting force calculation unit that calculates, on a basis of a first detected value by a first force sensor provided on one side of a rod-shaped member, at least one of acting forces on a first point of action and a second point of action that differ from each other on an other side of the rod-shaped member.

15 Claims, 10 Drawing Sheets

(51) Int. Cl.
  *B25J 3/00* (2006.01)
  *B25J 19/02* (2006.01)
  *A61B 34/37* (2016.01)
  *B25J 9/16* (2006.01)
  *B25J 13/08* (2006.01)
  *A61B 34/00* (2016.01)
  *A61B 90/00* (2016.01)

(52) U.S. Cl.
  CPC .......... *B25J 9/1633* (2013.01); *B25J 13/085* (2013.01); *B25J 19/02* (2013.01); *A61B 2090/064* (2016.02); *A61B 2090/065* (2016.02)

(58) Field of Classification Search
  CPC .......... B25J 3/00; B25J 9/1633; B25J 13/085; B25J 19/02
  USPC ................................................ 700/245, 258
  See application file for complete search history.

(56) References Cited

U.S. PATENT DOCUMENTS

| | | | | |
|---|---|---|---|---|
| 2013/0237766 A1* | 9/2013 | Pell | ........................ | A61B 7/00 600/211 |
| 2014/0076058 A1* | 3/2014 | Brugger | ................ | G01L 9/0041 73/723 |
| 2015/0157191 A1* | 6/2015 | Phee | ..................... | B25J 9/1674 600/106 |
| 2015/0157409 A1 | 6/2015 | Onuma | | |

FOREIGN PATENT DOCUMENTS

| | | |
|---|---|---|
| JP | 2005-329476 A | 12/2005 |
| JP | 2008-6517 A | 1/2008 |
| JP | 2008-006517 A | 1/2008 |
| JP | 2008-238338 A | 10/2008 |
| JP | 5327687 B2 | 10/2013 |
| JP | 2014-000118 A | 1/2014 |
| JP | 2014-118 A | 1/2014 |
| JP | 5458122 B2 | 4/2014 |
| JP | 2014-090800 A | 5/2014 |
| JP | 2014-90800 A | 5/2014 |
| JP | 2015-100677 A | 6/2015 |
| WO | 2008/123200 A1 | 10/2008 |
| WO | 2013/187011 A1 | 12/2013 |
| WO | 2014/069003 A1 | 5/2014 |
| WO | 2015/079775 A1 | 6/2015 |

OTHER PUBLICATIONS

International Preliminary Report on Patentability of PCT Application No. PCT/JP2015/075489, dated Apr. 20, 2017, 10 pages of English Translation and 05 pages of IPRP.

* cited by examiner

INFORMATION PROCESSING DEVICE, INFORMATION PROCESSING METHOD, AND PROGRAM

CROSS REFERENCE TO RELATED APPLICATIONS

This application is a U.S. National Phase of International Patent Application No. PCT/JP2015/075489 filed on Sep. 8, 2015, which claims priority benefit of Japanese Patent Application No. JP 2014-207980 filed in the Japan Patent Office on Oct. 9, 2014. Each of the above-referenced applications is hereby incorporated herein by reference in its entirety.

TECHNICAL FIELD

The present disclosure relates to an information processing device, an information processing method, and a program.

BACKGROUND ART

Recently, in the medical field, surgeries conducted using a support arm device are being conducted widely. For example Patent Literature 1 discloses a medical support arm device of what is called the master-slave type, in which an arm unit with a surgical tool (surgical instrument) attached is driven by the operations of an operator (a surgeon, for example) via a controller.

On the other hand, with a medical support arm device of the master-slave type as described in Patent Literature 1, technology for detecting force acting on the surgical instrument and transmitting such force to the operator operating the controller, or in other words, technology for precisely realizing force sensing and force feedback, has not been established. One of the reasons for this is because it is difficult to install on the leading edge section of a surgical instrument a force sensor for detecting force acting on the leading edge section. For example, consider forceps used in laparoscopic surgery. Only a narrow space with a diameter of approximately 5 (mm) exists at the leading edge section of the forceps, and it is difficult to mount in this space a high-precision force sensor, such as a six-axis force sensor, for example.

Accordingly, there has been developed technology that drives the arm unit of a support arm device with a pneumatic actuator, and also estimates the force acting on a surgical instrument attached to the arm unit based on the driving force of the pneumatic actuator, thereby providing force feedback (for example, Patent Literature 2). According to this technology, the force acting on the surgical instrument may be estimated without using a force sensor, thereby making it possible to address the issue related to the installation position of a force sensor as discussed above.

CITATION LIST

Patent Literature

Patent Literature 1: JP 5458122B
Patent Literature 2: JP 5327687B

DISCLOSURE OF INVENTION

Technical Problem

However, with the technology that uses a pneumatic actuator as described in Patent Literature 2, it is necessary to install in the operating room an air compressor for driving the pneumatic actuator, possibly producing loud noise or the like during surgery. Also, with force sensing and force feedback using such technology, it is considered that adequate precision has not yet been obtained from the perspective of responsiveness and reproducibility.

Accordingly, the present disclosure proposes a new and improved information processing device, information processing method, and program capable of detecting the force acting on a surgical instrument with a simpler configuration.

Solution to Problem

According to the present disclosure, there is provided an information processing device including: an acting force calculation unit that calculates, on a basis of a first detected value by a first force sensor provided on one side of a rod-shaped member, at least one of acting forces on a first point of action and a second point of action that differ from each other on an other side of the rod-shaped member.

In addition, according to the present disclosure, there is provided an information processing method including: calculating, by a processor, on a basis of a first detected value by a first force sensor provided on one side of a rod-shaped member, at least one of acting forces on a first point of action and a second point of action that differ from each other on an other side of the rod-shaped member.

In addition, according to the present disclosure, there is provided a program causing a processor of a computer to realize: a function of calculating, on a basis of a first detected value by a first force sensor provided on one side of a rod-shaped member, at least one of acting forces on a first point of action and a second point of action that differ from each other on an other side of the rod-shaped member.

According to the present disclosure, on the basis of a first detected value by a first force sensor provided on one side of a rod-shaped member, at least one of the acting forces on a first point of action and a second point of action that differ from each other on the other side of the rod-shaped member is calculated. Consequently, with a comparatively simple configuration of providing a force sensor on one side of a surgical instrument (for example, the base side), it becomes possible to compute the force acting on the other side of the surgical instrument (for example, the leading edge side).

Advantageous Effects of Invention

According to the present disclosure as described above, it becomes possible to detect a force acting on a surgical instrument with a simpler configuration. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
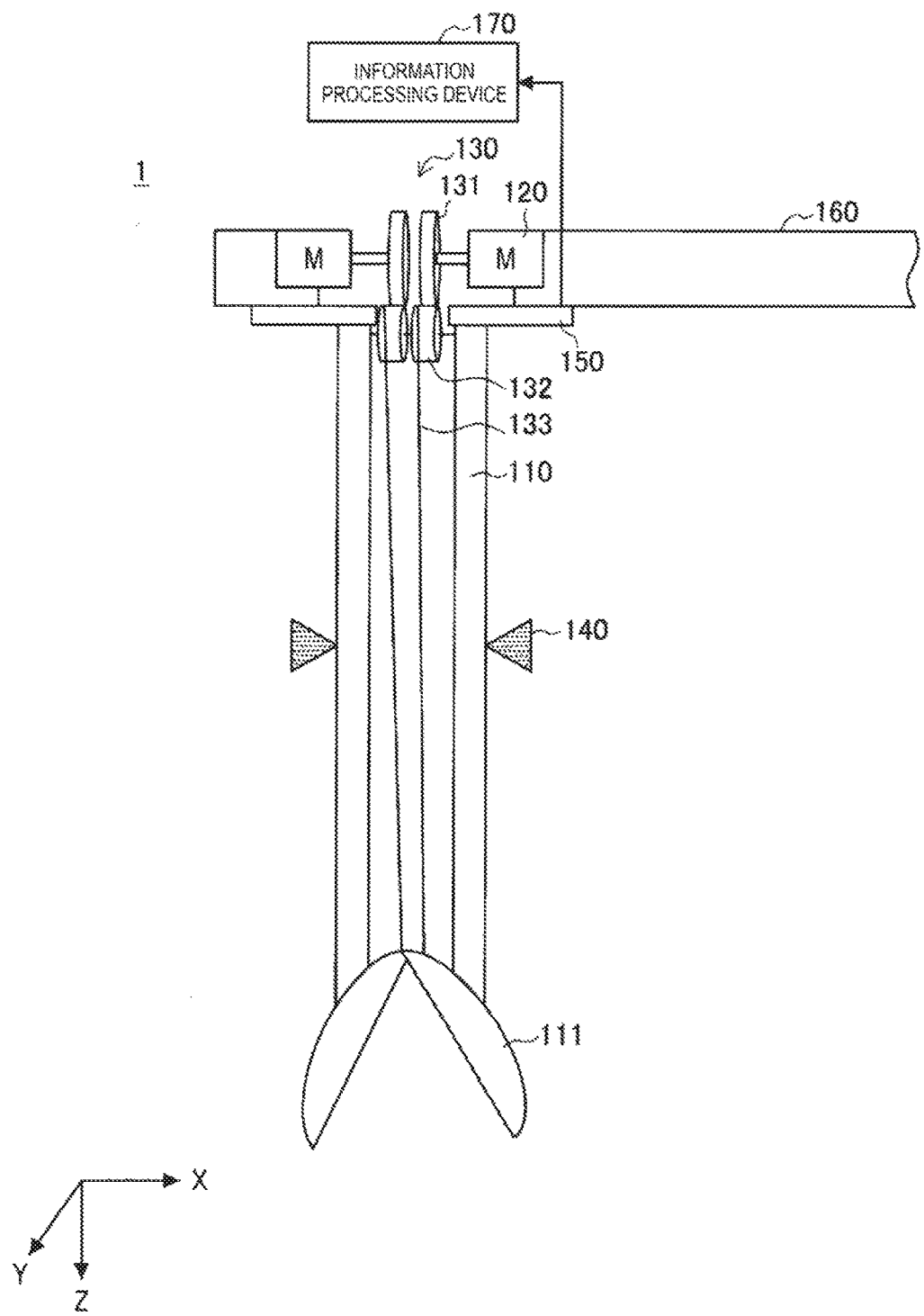
FIG. 1 is a diagram illustrating a diagrammatic configuration of a system according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. First Embodiment
1-1. Configuration of system
1-2. Acting force calculation method
1-3. Functional configuration
1-4. Information processing method
2. Second Embodiment
2-1. Configuration of system
2-2. Acting force calculation method
2-3. Functional configuration
2-4. Information processing method
3. Modifications
3-1. Modification of first embodiment
3-2. Modification of second embodiment
3-3. Modification in which six-axis force sensor is used instead of torque sensor
4. Hardware configuration
5. Supplement Herein, in the first and second embodiments of the present disclosure described below, the force acting on a surgical instrument attached to an arm unit of a medical support arm device is detected, or in other words, force sensing is conducted. In the following description, as an example of the first and second embodiments, a case is described in which the support arm device is used for endoscopic surgery, particularly laparoscopic surgery, and the surgical instrument is forceps. In laparoscopic surgery, multiple openings having a size approximately from 5 (mm) to 10 (mm) are made in the patient's body, surgical instruments such as a laparoscope, electrosurgical instrument, and forceps are inserted respectively through these openings, and while observing the surgical site with the laparoscope, treatment is performed on the surgical site with the other surgical instruments. In this way, since laparoscopic surgery requires delicate work to be performed by inserting narrow forceps into the patient's body, in cases where the operation of the forceps is performed manually, there is a possibility that the success rate of the surgery may be greatly influenced by the surgical skill of the operator (surgeon). By using a support arm device for laparoscopic surgery like in the first and second embodiments, the difficulty of the surgery is lowered greatly, making it possible to perform the surgery safely.

In the first and second embodiments, the force acting on a rod-shaped member such as forceps may be detected favorably. However, the present disclosure is not limited to such an example, and the technique for detecting the force acting on a surgical instrument according to the present disclosure is applicable to any surgical instrument, insofar as the instrument is a rod-shaped member. Note that in the following description, unless specifically noted otherwise, expressions referring to the force acting on a surgical instrument encompass one or both of the force and the moment.

In addition, the support arm device according to the first and second embodiments may be equipped with a function of controlling the driving of the arm unit based on the detected force acting on the surgical instrument. For example, if the detected force acting on the surgical instrument exceeds a certain threshold value, the arm unit may be controlled to inhibit the movement of the surgical instrument, so that the surgical instrument does not move any farther in that direction. Consequently, it becomes possible to prevent a situation in which excessive force is imparted to tissue inside the patient's body cavity due to contact with the surgical instrument.

In addition, the support arm device according to the first and second embodiments may also be a support arm device of what is called the master-slave type, which is operated remotely by the operator via a controller. In this case, the support arm device may be equipped with what is called a force feedback function, which transmits the detected force acting on the surgical instrument to the operator via the controller.

However, the configuration characteristic to the first and second embodiments of the present disclosure is a configuration for conducting force sensing, and various known types of configurations may be applied as the configuration for conducting drive control of the arm unit or as the configuration for realizing force feedback. Consequently, in the following, detailed description will be omitted regarding the configuration for conducting various types of control using the detected force, and the configuration for conducting force sensing will be described primarily.

1. First Embodiment (1-1. Configuration of System)

A diagrammatic configuration of a system according to the first embodiment of the present disclosure will be described with reference to FIG. 1. FIG. 1 is a diagram illustrating a diagrammatic configuration of a system according to the first embodiment of the present disclosure.

In FIG. 1, only the configuration in the vicinity of the connecting section between the arm unit and the surgical instrument of the support arm device according to the first embodiment is illustrated. Referring to FIG. 1, the system 1 according to the first embodiment is equipped with forceps 110 attached to an arm unit 160, a motor 120 for driving the forceps 110, a transmission member 130 that transmits the driving force of the motor 120 to the leading edge section of the forceps 110, a trocar 140 that acts as a guide when inserting the forceps 110 inside the patient's body, a force sensor 150 provided on the connecting section between the forceps 110 and the arm unit 160, and an information processing device 170 that calculates the force acting on the forceps 110 based on detected values from the force sensor 150.

The arm unit 160 may have a multi-link structure in which multiple links are joined to each other by joint sections. In FIG. 1, only one link constituting the arm unit 160 is illustrated diagrammatically. The support arm device according to the first embodiment is able to drive the arm unit 160 according to any of various known control methods, such as position control and force control, with a control device not illustrated. Additionally, the control device is able to cause the forceps 110 to operate by causing the motor 120 to drive. Since any of various known control techniques used in typical support arm devices may be applied to the drive control of the arm unit 160 and the control of the operation of the forceps 110, detailed description is omitted herein.

The forceps 110 are a rod-shaped member, on the leading edge of which is provided a grip unit 111 that includes an openable and closable scissor-like configuration. During surgery, the forceps 110 are inserted into the patient's body cavity, and the grip unit 111 is used to put pressure on a blood vessel in the surgical site, or grip excised tissue or the like. Note that the type of the forceps 110 is not limited, and the forceps 110 may be any type of forceps. Specifically, when inserting the forceps 110 into a body cavity, first, the trocar 140 is inserted into an opening having a size approximately from 5 (mm) to 10 (mm) made in the patient's body. The trocar 140 is a hollow cylindrical member, and the forceps 110 is inserted into the patient's body cavity by passing through the interior of the trocar 140.

At this point, consider the force which may act on the forceps 110 from the outside during surgery. Since the leading edge section of the forceps 110 may contact body tissue inside the patient's body cavity, there is a possibility that the forceps 110 may be subjected to force at the site of contact with the body tissue. Also, since the outer circumference of the forceps 110 may contact the inner wall of the trocar 140, there is a possibility that the forceps 110 may be subjected to force at the site of contact with the inner wall of the trocar 140. In this way, forces from two different sites may act on the forceps 110. In the following description, in the forceps 110, the point subjected to force due to contact with body tissue inside the patient's body cavity is also designated the first point of action, while the point subjected to force due to contact with the inner wall of the trocar 140 is also designated the second point of action.

The first point of action may be the leading edge of the forceps 110 as discussed above. On the other hand, in a state in which external force is not being exerted on the trocar 140, and the forceps 110 is simply inserted into the trocar 140, the force acting on the forceps 110 from the inner wall of the trocar 140 is not very large. The case in which a larger force may act on the forceps 110 from the inner wall of the trocar 140 is a case in which a force is acting on the trocar 140 from the outside. This is because if a force acts on the trocar 140 from the outside, that force is also transmitted via the lateral wall of the trocar 140 to the forceps 110 inserted inside. Consequently, from among the sites where the forceps 110 is inserted into the trocar 140, the second point of action may be a point at which a force acts on the trocar 140 from the outside.

Considering the purpose of the trocar 140, the outer wall of the trocar 140 contacts the perimeter of the opening made in the patient's body. Consequently, movement of the patient's body due to respiration or the like causes a force to act on the trocar 140 from the outside at the site of contact. In this way, the second point of action is a site of contact between the inner wall of the trocar 140 and the forceps 110 at a position where the perimeter of the opening made in the patient's body contacts the outer wall of the trocar 140. The second point of action may also be considered to be a position corresponding to the vicinity of the patient's body surface.

Note that in the first embodiment, any of various known types of trocars may be used as the trocar 140. Consequently, in FIG. 1, to keep the drawing from becoming complicated, illustration of the detailed structure of the trocar 140 has been omitted. Instead, for the sake of explanation, FIG. 1 diagrammatically illustrates only the site of contact between the forceps 110 and the trocar 140, which corresponds to the second point of action.

As illustrated, at the section of the arm unit 160 where the forceps 110 is attached, the motor 120 for driving the forceps 110 is provided. In the example illustrated in FIG. 1, two of the motor 120 are provided for the forceps 110. The forceps 110 operates as a result of the driving force of the motor 120 being transmitted to the forceps 110 via the transmission member 130.

The transmission member 130 is made up of gears 131 and 132, and a wire 133. The center of the gear 131 is axially supported by the drive shaft of the motor 120, and rotates in conjunction with the driving of the motor 120. The gear 131 engages with the gear 132, whose size is adjusted to achieve a certain gear reduction ratio, for example. One end of the wire 133 is wound around the gear 132, and configured so that tensile force is exerted on the wire 133 by the motor 120 via the gears 131 and 132. The forceps 110 is configured to be hollow, with the wire 133 extending through the interior of the forceps 110. The other end of the wire 133 is connected to the grip unit 111 on the leading edge of the forceps 110, and as a result of the wire 133 being driven by the motor 120, operations such as the opening and closing of the grip unit 111 are conducted. Note that in cases in which the forceps 110 includes another movable section other than the grip unit 111, such as a joint, for example, the other movable section may also be driven by the wire 133.

Herein, the gears 131 and 132 may also not necessarily be provided, and the forceps 110 may be driven by connecting the wire 133 directly to the drive shaft of the motor 120. However, by using a transmission member like the gears 131 and 132, work such as maintenance and replacement of the arm unit 160 and the forceps 110 becomes easier. Also, the specific configuration of the transmission member 130 likewise is not limited to the illustration, and may have an arbitrary configuration insofar as the configuration enables the transmission member 130 to transmit the driving force of the motor 120 to the wire 133.

Note that in the example illustrated in FIG. 1, the mechanism that causes the forceps 110 to operate is configured by two of the wire 133 being driven respectively by two of the motor 120, but the mechanism that causes the forceps 110 to operate is not limited to such an example. The disposed number and disposed position of the motor 120 as well as the specific configuration of the transmission member 130 may be set appropriately so that the desired operation of the forceps 110 is realized.

The force sensor 150 is provided at the connecting section between the arm unit 160 and the forceps 110. In the example illustrated in FIG. 1, one force sensor 150 having a ring shape is provided. In FIG. 1, a cross-section of the force sensor 150 is illustrated. As illustrated, the forceps 110 is connected to the arm unit 160 via the force sensor 150, and the force sensor 150 is able to detect the forces and the moments acting on the forceps 110. The force sensor 150 is a six-axis force sensor, for example, and includes a function of detecting force in three mutually orthogonal axis directions and the moment about the three axis directions. In this way, in the first embodiment, the force sensor 150 is provided on one end of the forceps 110, while the first point of action and the second point of action exist on the side of the other end.

Note that the disposed number and disposed position of the force sensor 150 is not limited to the example illustrated in the drawing. In the first embodiment, it is sufficient for the force sensor 150 to be provided on a different side from the first point of action and the second point of action, and the specific disposed number and disposed position may be set arbitrarily so that the calculation of the forces acting on the first point of action and/or the second point of action of the forceps 110 by the information processing device 170 discussed later is executed precisely.

Herein, in the following description, the extension direction of the forceps 110, which is a rod-like member, is defined to be the z-axis direction. Also, the two mutually orthogonal directions to the z-axis direction are defined to be the x-axis direction and the y-axis direction. In the first embodiment, the force sensor 150 is disposed so that the x-axis direction, the y-axis direction, and the z-axis direction are the detection axes.

Information about the forces and moments detected by the force sensor 150 is transmitted to the information processing device 170. The information processing device 170 calculates the acting forces on the first point of action and/or the second point of action of the forceps 110 (hereinafter also designated simply the acting force on the forceps 110), based on detected values from the force sensor 150. For example, the force sensor 150 is configured to detect the forces and moments on a certain interval, and transmit information about the detected values to the information processing device 170 continually. The information processing device 170 is able to calculate the acting force on the forceps 110 continually on a certain interval, in accordance with the detection interval of the force sensor 150. Note that details about the calculation process conducted by the information processing device 170 will be described further in (1-2. Acting force calculation method) and (1-3. Functional configuration) below. Additionally, the method of communication between the force sensor 150 and the information processing device 170 may be wired or wireless, and any of various known types of communication schemes may be applied thereto.

Herein, it is sufficient for the information processing device 170 to operate according to a certain program and include a function of conducting the calculation process discussed above, whereas the specific configuration is not limited. For example, the information processing device 170 may be a general-purpose information processing device such as a personal computer (PC), or an information processing device specialized in numerical calculation, such as a computational server. Alternatively, the information processing device 170 may be any of various types of processors, such as a central processing unit (CPU) or a digital signal processor (DSP), and may also be what is called a microcontroller, in which a processor and a storage device such as memory are configured in an integrated manner. Also, the information processing device 170 may be configured in an integrated manner with a control device that controls the driving of the support arm device.

Furthermore, the information processing device 170 may not necessarily be a single device, but instead may be configured by multiple devices, and the calculation process discussed above may be conducted by cooperative action among the multiple devices. For example, the calculation process may be conducted in parallel by multiple devices to improve the calculation speed. Additionally, the information processing device 170 may also not be disposed near the support arm device, but instead be provided on a network (also referred to as in the cloud), for example, and may conduct the calculation process discussed above by receiving detected values from the force sensor 150 via the network.

The above thus describes a diagrammatic configuration of the system 1 according to the first embodiment with reference to FIG. 1.

(1-2. Acting Force Calculation Method)

Figure 2:
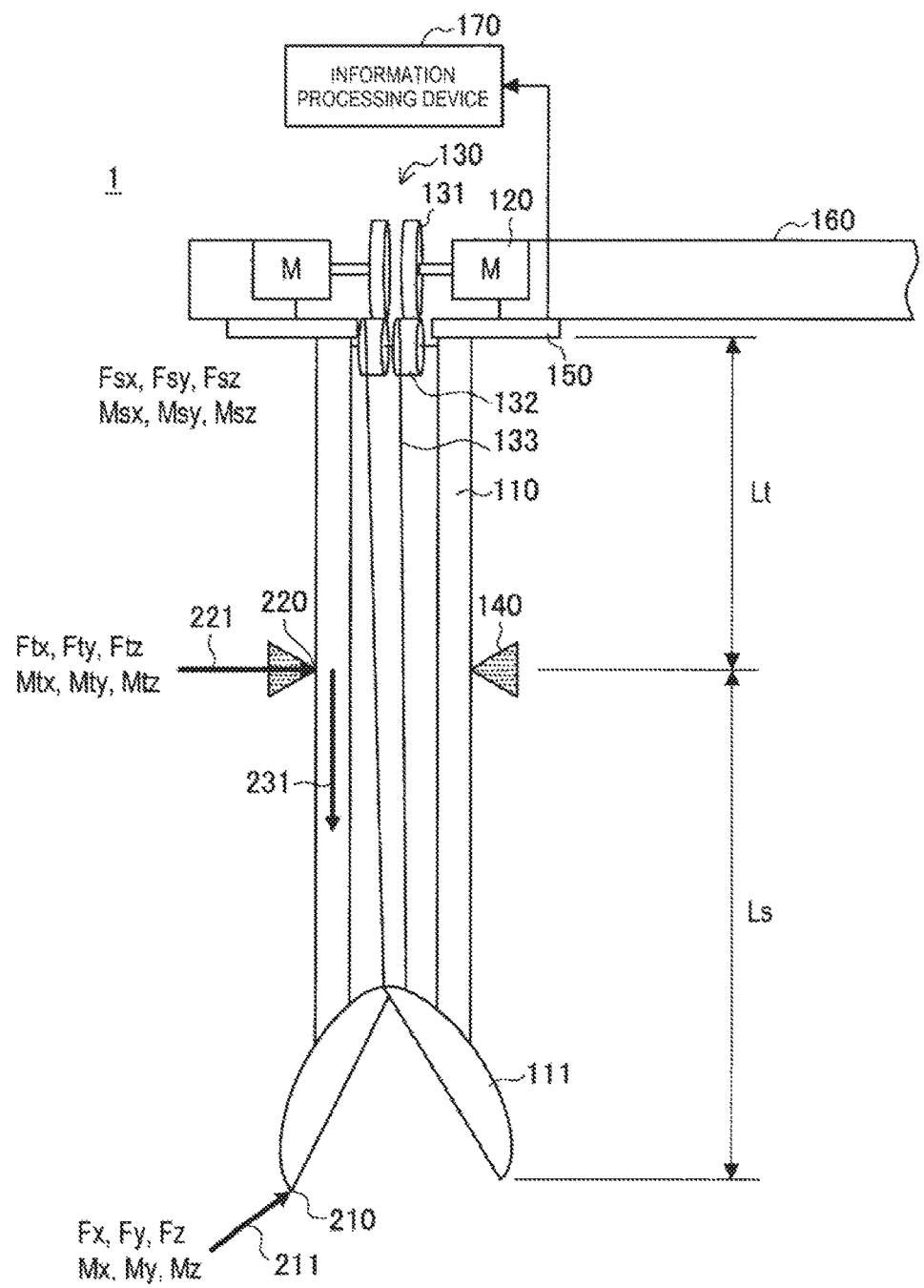
FIG. 2 is an explanatory diagram for explaining a method of calculating acting forces on a first point of action and/or a second point of action of forceps in a first embodiment.

A method of calculating the acting forces on the first point of action and/or the second point of action of the forceps 110 executed in the information processing device 170 discussed above will be described with reference to FIG. 2. FIG. 2 is an explanatory diagram for explaining a method of calculating the acting forces on a first point of action and/or a second point of action of the forceps 110 in the first embodiment. Note that FIG. 2 corresponds to FIG. 1 with the addition of arrows expressing the forces acting on the forceps 110 and a labeling of the dimensions and the like of the forceps 110. For this reason, duplicate description will be reduced or omitted regarding the configuration already described with reference to FIG. 1.

Herein, in the first embodiment, to compute the acting forces on the forceps 110, for the sake of simplicity, forces acting on the forceps 110 due to the forceps 110 driving (hereinafter also designated active forces) will not be considered. In other words, the first embodiment may also be said to assume that the forceps 110 is not moving and in a still state. In this way, it is still possible to compute the acting forces on the forceps 110 with some degree of accuracy, even when active forces are not considered. Note that a more precise acting force calculation method that accounts for active forces will be described in detail in (2. Second embodiment) below. The first embodiment, although having a risk of somewhat lowered accuracy compared to the second embodiment discussed later, makes it possible to compute the acting forces on the forceps 110 with a simpler configuration.

As illustrated in FIG. 2, when active forces are not considered, there may act on the forceps 110 a force 211 with respect to the first point of action 210, a force 221 with respect to the second point of action 220, and a gravitational force 231 due to the weight of the forceps 110 itself. The force 211 is the reaction force imparted to the leading edge of the forceps 110 from a body tissue inside the patient's body cavity due to the leading edge of the forceps 110 contacting the body issue. Also, the force 221 is the force imparted to the trocar 140 contacting the perimeter of the opening made in the patient's body due to the motion of the patient's body from respiration and the like, which is then transmitted to the forceps 110 via the lateral wall of the trocar 140.

For the sake of explanation, hereinafter, the forces acting in the x-axis direction, the y-axis direction, and the z-axis direction at the first point of action 210 will be designated Fx, Fy, and Fz, respectively. Also, the moments about the x-axis direction, the y-axis direction, and the z-axis direction acting at the first point of action 210 will be designated Mx, My, and Mz, respectively. Also, similarly, the forces acting in the x-axis direction, the y-axis direction, and the z-axis direction at the second point of action 220 will be designated Ftx, Fty, and Ftz, respectively. Also, the moments about the x-axis direction, the y-axis direction, and the z-axis direction acting at the second point of action 220 will be designated Mtx, Mty, and Mtz, respectively. Furthermore, of the detected values from the force sensor 150, the detected values of the forces in the x-axis direction, the y-axis direction, and the z-axis direction will be designated Fsx, Fsy, and Fsz, respectively, while the detected values of the moments about the x-axis direction, the y-axis direction, and the z-axis direction will be designated Msx, Msy, and Msz, respectively.

Note that, as discussed earlier, in the present embodiment, the disposed number and disposed position of the force sensor 150 is not limited to the example configuration illustrated in FIG. 1. For example, multiple force sensors 150 may also be provided at the connecting section between the arm unit 160 and the forceps 110. In the case of providing multiple force sensors 150, values obtained by combining the detected values from these multiple force sensors 150 or the like may be treated as Fsx, Fsy, Fsz, Msx, Msy, and Msz.

Herein, the mass of the forceps 110 is a known quantity measurable in advance. Also, the positions and the orientations of the arm unit 160 and the forceps 110 are stored by the control device that controls the driving of the arm unit 160 as an internal model, for example (the mass of the forceps 110 may also be stored as the internal model). Consequently, the magnitude of the gravitational force 231 acting on the forceps 110 and the magnitude of the moment caused by the gravitational force 231 depending on the position and the orientation of the forceps 110 may be treated as known values calculable on the basis of the information about the positions and the orientations of the arm unit 160 and the forceps 110 stored by the control device. Consequently, in the first embodiment, the values obtained by subtracting the component due to the gravitational force 231 from the detected values from the force sensor 150 may be treated as Fsx, Fsy, Fsz, Msx, Msy, and Msz. Consequently, in the following calculations, it is not necessary to consider the gravitational force 231 or the moment due to the gravitational force 231.

Herein, in the first embodiment, when calculating the acting forces on the forceps 110, constraint conditions are set depending on the usage mode of the forceps 110. The constraint conditions may be set appropriately by a person such as the operator or a designer of the system 1, in light of the usage mode of the forceps 110 according to the details of the surgery or the like.

First, at the site of contact between the trocar 140 and the forceps 110 (that is, the second point of action 220), it is supposed that the force Ftz in the z-axis direction, the moment Mtx about the x-axis, the moment Mty about the y-axis, and the moment Mtz about the z-axis are not acting or acting very little on the forceps 110. This is because the forceps 110 is inserted inside the trocar 140 which is a hollow cylindrical member, and the second point of action is the site of contact between the outer circumferential section of the forceps 110 and the inner wall of the trocar 140. Thus, structurally, it is supposed that the force Ftz and the moments Mtx, Mty, and Mtz are sufficiently small values compared to the other forces and moments. Consequently, as a first constraint condition, the force Ftz and the moments Mtx, Mty, and Mtz at the second point of action 220 are treated as being approximately zero.

In addition, since the first point of action 210 is the leading edge of the forceps 110 which is a rod-shaped member, it is supposed that the moments about axes other than the extension direction of the forceps 110, or in other words the z-axis direction, are not acting or acting very little at the first point of action 210. Consequently, as a second constraint condition, the moments Mx and My at the first point of action 210 are treated as being approximately zero.

Under the above constraint conditions, if the equilibrium of the forces and the moments among the detected values Fsx, Fsy, Fsz, Msx, Msy, and Msz from the force sensor 150 (after subtracting the component of the gravitational force 231), Fx, Fy, Fz, Mx, My, and Mz at the first point of action 210, and Ftx, Fty, Ftz, Mtx, Mty, and Mz at the second point of action 220 are considered, the following formulas (1) to (6) may be obtained. Note that the formulas (4) to (6) below are derived from the equilibrium of the moments centered on the second point of action.

[Math. 1]
$$Fsx+Ftx+Fx=0 \qquad (1)$$

[Math. 2]
$$Fsy+Fty+Fy=0 \qquad (2)$$

[Math. 3]
$$Fsz+Fz=0 \qquad (3)$$

[Math. 4]
$$-Fsx \times Lt + Msy + Fx \times Ls = 0 \qquad (4)$$

[Math. 5]
$$Fsy \times Lt + Msx - Fy \times Ls = 0 \qquad (6)$$

[Math. 6]
$$Msz=Ms \qquad (6)$$

Note that Lt is the distance from the force sensor 150 to the second point of action 220, and Ls is the distance from the second point of action 220 to the leading edge of the forceps 110.

Herein, in the above formulas (1) to (6), Fsx, Fsy, Fsz, Msx, Msy, and Msz are values obtained from the force sensor 150, and are known values. In addition, Lt and Ls are also known values. The reason for this is because Lt and Ls may be calculated easily from the total length of the forceps 110, and the positional relationship between the trocar 140 and the forceps 110. Specifically, the total length of the forceps 110 is obviously a known value from the structure of the forceps 110, and information about the length of the forceps 110 is also included in the internal model used when the control device of the support arm device controls the driving of the arm unit 160, for example. In addition, during surgery, the trocar 140 is inserted into the patient, and thus its position is mostly fixed, and position information about the trocar 140 is also included in the above internal model. Furthermore, as discussed above, position information about the forceps 110 is included in the above internal model. Consequently, since the total length of the forceps 110 and the positional relationship between the trocar 140 and the forceps 110 are ascertained by the control device, Lt and Ls may be treated as known values.

In this way, the unknown quantities in the formulas (1) to (6) are just the six quantities Fx, Fy, Fz, Mz, Ftx, and Fty. Since the number of formulas matches the number of unknown quantities, by solving the simultaneous equations made up of the formulas (1) to (6), Fx, Fy, Fz, Mz, Ftx, and Fty may be computed. In the first embodiment, the information processing device 170 computes Fx, Fy, Fz, Mz, Ftx, and Fty by solving the simultaneous equations made up of the formulas (1) to (6).

For example, the information processing device 170 is able to solve the above simultaneous equations by various numerical calculation techniques. Since any of various known techniques may be used as the numerical calculation technique for solving the simultaneous equations, detailed description is omitted herein.

Alternatively, in a case in which the usage mode of the forceps 110 changes little or not at all, and the constraint conditions are fixed, an analytical solution to the simultaneous equations may be calculated in advance by a person such as the operator or a designer of the system 1, and input into the system 1. For example, by solving for the unknown quantities in the simultaneous equations made up of the above formulas (1) to (6), the following formulas (7) to (12) may be obtained as an analytical solution. The information processing device 170 is able to substitute the detected values from the force sensor 150, namely Fsx, Fsy, Fsz, Msx, Msy, and Msz, as well as Lt and Ls which are calculable as known quantities, into the formulas (7) to (12) below), and thereby compute Fx, Fy, Fz, Mz, Ftx, and Fty.

[Math. 7]
$$Fx = \frac{Fsx \times Lt - Msy}{Ls} \quad (7)$$

[Math. 8]
$$Fy = \frac{Msx + Fsy \times Lt}{Ls} \quad (8)$$

[Math. 9]
$$Fz = -Fsz \quad (9)$$

[Math. 10]
$$Mz = Msz \quad (10)$$

[Math. 11]
$$Ftx = \frac{Fsx \times (Lt + Ls) - Msy}{Ls} \quad (11)$$

[Math. 12]
$$Fty = \frac{Msx + Fsy \times (Lt + Ls)}{Ls} \quad (12)$$

The above thus describes a method of calculating the acting forces according to the first embodiment. As described above, in the first embodiment, the acting forces on the first point of action 210 and/or the acting forces on the second point of action of the forceps 110 are calculated based on equilibrium formulas of the detected values from the force sensor 150, the acting forces on the first point of action 210, and the acting forces on the second point of action. At this point, by setting constraint conditions for the acting forces on the forceps 110 according to the usage mode of the forceps 110, and simplifying the above equilibrium formulas based on the constraint conditions, the acting forces on the first point of action 210 and/or the acting forces on the second point of action of the forceps 110 are calculated.

Herein, the constraint conditions are not limited to the examples discussed above. In the above embodiment, constraint conditions as discussed above are provided to calculate the forces acting on the forceps 110 used in laparoscopic surgery, but different constraint conditions may also be set depending on the type of the forceps 110 and the usage method. Also, as described at the beginning, in the first embodiment, the target for which acting forces are calculated is not limited to the forceps 110, and the acting forces on any other type of rod-shaped member may also be calculated. Since the usage mode may also vary depending on the member, in the first embodiment, suitable constraint conditions are set appropriately by a person such as a user and a designer of the system 1, according to the usage mode of the member for which the acting forces are to be calculated. Even if the constraint conditions are different, it is still possible to calculate the forces acting on a member by simplifying the equilibrium formulas of the forces and moments based on the constraint conditions, similarly to the method discussed above.

(1-3. Functional Configuration)

Figure 3:
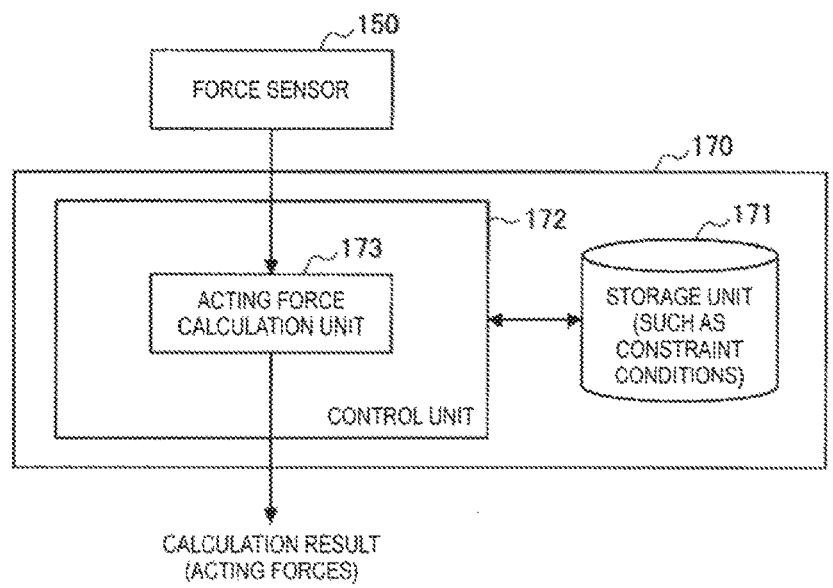
FIG. 3 is a block diagram illustrating a functional configuration of an information processing device according to a first embodiment.

Next, a functional configuration of the information processing device 170 that executes the calculation process described above will be described with reference to FIG. 3. FIG. 3 is a block diagram illustrating a functional configuration of the information processing device 170 according to the first embodiment.

Referring to FIG. 3, the information processing device 170 according to the first embodiment is equipped with a storage unit 171 and a control unit 172. As illustrated, the information processing device 170 is connected to the force sensor 150, enabling the communication of various types of information. The information processing device 170 is able to acquire, from the force sensor 150, information about detected values detected by the force sensor 150 (that is, forces and moments). Note that, although omitted from illustration, the information processing device 170 is also connected to the control device that controls the driving of the arm unit 160, enabling the communication of various types of information. The information processing device 170 is able to acquire, from the control device, information such as information about the positions and the orientations of the arm unit 160 and the forceps 110, and information necessary to calculate Lt and Ls discussed above.

The storage unit 171 is made up of any of various types of storage devices, such as a magnetic storage device like a hard disk drive (HDD), a semiconductor storage device, an optical storage device, or a magneto-optical storage device, for example, and stores various information processed by the control unit 172 and the results of processes by the control unit 172. The control unit 172 is able to execute various processes by utilizing the various information stored in the storage unit 171.

In the first embodiment, the storage unit 171 stores various information necessary to perform the calculations described in (1-2. Acting force calculation method) above. For example, the storage unit 171 stores detected values from the force sensor 150. As another example, the storage unit 171 stores various information transmitted from the above control device (such as information about the positions and the orientations of the arm unit 160 and the forceps 110, information about the shape, mass, and the like of the forceps 110), and information about the position of the trocar 140, for example). As another example, the storage unit 171 stores information about the constraint conditions discussed above. Note that information about the constraint conditions may be input into the storage unit 171 in advance by a person such as the operator or a designer of the system 1, prior to surgery.

The control unit 172 is made up of any of various types of processors, such as a CPU or a DSP, for example, and centrally controls various processes in the information processing device 170. The control unit 172 includes an acting force calculation unit 173 as a function. Note that the respective functions of the control unit 172 may be realized by having any of various types of processors constituting the control unit 172 operate by following a certain program.

Information about detected values is input from the force sensor 150 into the acting force calculation unit 173. The acting force calculation unit 173 calculates the acting forces on the first point of action and/or the second point of action of the forceps 110, based on detected values from the force sensor 150. Specifically, the acting force calculation unit 173 performs the calculations described in (1-2. Acting force calculation method) above, based on detected values from the force sensor 150 and various information stored in the storage unit 171, and calculates the acting forces on the forceps 110.

More specifically, the acting force calculation unit 173 establishes mathematical formulas expressing the equilibrium of forces and the equilibrium of moments as indicated in the above formulas (1) to (6), based on constraint conditions stored in the storage unit 171. At this point, the acting force calculation unit 173 is provided with detected values from the force sensor 150. In addition, the acting force calculation unit 173 is able to calculate the component of the gravitational force acting on the forceps 110 or Lt and Ls discussed above based on information about the forceps 110, information indicating the positions and the orientations of the arm unit 160, and the like stored in the storage unit 171. The acting force calculation unit 173 substitutes known values such as the detected values from the force sensor 150 after subtracting the gravitational force component, Lt, and Ls into the established mathematical formulas, and then treats these mathematical formulas as simultaneous equations to solve for the unknown quantities (in other words, the acting forces on the forceps 110). At this point, in a case in which the usage mode of the forceps 110 changes little or not at all, and the constraint conditions are fixed, an analytical solution that has already solved the above simultaneous equations for the unknown quantities (for example, the above formulas (7) to (12)) may be calculated by a person such as the operator and a designer of the system 1, and stored in the storage unit 171. The acting force calculation unit 173 is able to calculate the acting forces on the forceps 110 by substituting known values such as the detected values from the force sensor 150 after subtracting the gravitational force component, Lt, and Ls into the analytical solution. Note that the detected values from the force sensor 150 may also be stored in the storage unit 171 temporarily after being transmitted to the information processing device 170, and the acting force calculation unit 173 may obtain detected values from the force sensor 150 to use in calculations by referencing the storage unit 171.

Note that the acting force calculation unit 173 may not necessarily compute all unknown quantities when solving the simultaneous equations including the above formulas (1) to (6), or when substituting known values into the above formulas (7) to (12). For example, if it is desirable to compute only the acting forces on the leading edge of the forceps 110 (in other words, the first point of action), the acting force calculation unit 173 may calculate only the unknown quantities corresponding to the acting forces at the first point of action. Which unknown quantities to compute may be set appropriately by a person such as the operator and a designer of the system 1.

The acting forces on the forceps 110 calculated by the acting force calculation unit 173 are transmitted to the above control device, for example. In the control device, control of the arm unit 160 and control of force feedback into the operator's controller are conducted based on the calculated acting forces on the forceps 110. Alternatively, calculation results by the acting force calculation unit 173 may be displayed on a display unit (not illustrated) or transmitted to other equipment via a communication unit (not illustrated), and output to the operator or the like in a format such as numerical values or graphs.

The above thus describes a functional configuration of the information processing device 170 with reference to FIG. 3. As described above, according to the first embodiment, on the basis of detected values from the force sensor 150 provided on one side of the forceps 110 (the connecting section that connects with the arm unit 160), at least one of the acting forces on a first point of action and a second point of action which differ from each other and which exist on the other side of the forceps 110 is calculated by the acting force calculation unit 173. Consequently, even if a force sensor is not provided on the leading edge of the forceps 110, the acting forces on the leading edge may be calculated. In this way, according to the first embodiment, it becomes possible to detect a force acting on the forceps 110 with a simpler configuration.

Since the force acting on the forceps 110 is detectable, the detected force may be used to diagnose the surgical site or further increase the safety of surgery. For example, on the basis of the detected acting forces on the forceps 110, it is possible to check the patient's condition by inspecting the hardness of the surgical site, or check the texture of a site that is inaccessible to a camera such as a laparoscope. As another example, on the basis of the detected acting forces on the forceps 110, it is possible to conduct drive control of the arm unit 160 to which the forceps 110 is attached so that a certain force or greater is not imparted to the surgical site, or when pulling an excised site out of the body, determine whether or not the excised site is caught on other tissue inside the body. In this way, the detected acting forces on the forceps 110 may be used for various purposes.

Herein, in the above description, the acting forces on the forceps 110 are calculated while taking the total length of the forceps 110 to be fixed. However, the first embodiment is not limited to such an example, and the length of the forceps 110 may also be variable. In a case in which the length of the forceps 110 is variable, the values of Lt and Ls may change according to the change in the length of the forceps 110. In the first embodiment, in a case in which the length of the forceps 110 is variable, the acting force calculation unit 173 is able to calculate Lt and Ls according to the change in the length of the forceps 110, and use the calculated Lt and Ls to calculate the acting forces on the first point of action and/or the second point of action. Specifically, a change in the length of the forceps 110 is ascertained by the control device that controls the driving of the arm unit 160 as the internal model, for example. Consequently, if the length of the forceps 110 changes, the acting force calculation unit 173 is able to recalculate Lt and Ls by acquiring information about the changed length of the forceps 110 from the control device.

Also, in the above description, the forceps 110 is treated as a rod-shaped member that extends approximately linearly. However, the first embodiment is not limited to such an example, and the forceps 110 may also include a joint section, and may be configured to have a variable shape and orientation. In this case, depending on the shape and the orientation of the forceps 110, the positions of the first point of action and the second point of action (that is, the values of Lt and Ls) and the center-of-gravity position of the forceps 110 (that is, the position at which the gravitational force acts) may change. In the first embodiment, if the forceps 110 includes a joint section, the acting force calculation unit 173 may calculate the positions of the first point of action, the second point of action, and the center of gravity according to the change in the shape and the orientation of the forceps 110, cause the calculated position information to be reflected in the above formulas (1) to (6), and calculate the acting forces on the first point of action and/or the second point of action. Specifically, if the forceps 110 includes a joint section, the driving of the joint section of the forceps 110 may be controlled by the control device that controls the driving of the arm unit 160. Consequently, changes in the shape or the orientation of the forceps 110 due to the joint section being driven are ascertained by the control device as the internal model, for example. Consequently, if the joint section drives, and the shape and the orientation of the forceps 110 change, the acting force calculation unit 173 is able to recalculate the positions of the first point of action, the second point of action, and the center of gravity by acquiring information about the changed position and orientation of the forceps 110 from the control device.

Note that in FIG. 3, for the sake of simplicity, only the functions characteristic of the first embodiment are illustrated, while other functions are omitted from illustration. The information processing device 170 additionally may include any of various functions included in a typical information processing device. For example, the information processing device 170 additionally may include functions such as an input unit that accepts various kinds of operating input from the user, an output unit that output various kinds of information visually or aurally to the user, and a communication unit that communicates with other external equipment.

In addition, the device configuration of the information processing device 170 is not limited to the example illustrated in FIG. 3. For example, the respective functions of the information processing device 170 illustrated in FIG. 3 may not necessarily be provided onboard a single device in an integrated manner. The respective functions provided onboard the information processing device 170 illustrated in FIG. 3 may also be provided onboard multiple devices in a distributed manner, and the information processing device 170 may be configured by communicably connecting these multiple devices. For example, the storage unit 171 may also be provided as external equipment different from the information processing device 170, and the information processing device 170 may execute the calculation process discussed above while communicating with the external equipment, namely the storage unit 171. As another example, the respective functions of the control unit 172 may be executed by a single processor, or may be executed by the cooperative action of multiple processors.

Additionally, it is possible to develop a computer program for realizing the functions of the information processing device 170 according to the first embodiment as discussed above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

(1-4. Information Processing Method)

Figure 4:
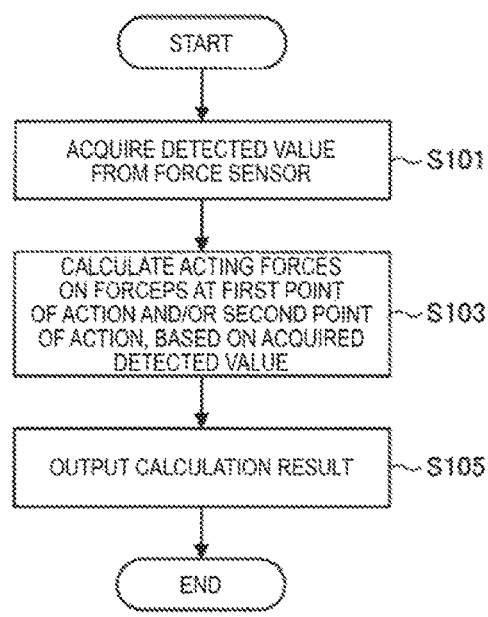
FIG. 4 is a flowchart illustrating an example of a processing procedure of an information processing method according to a first embodiment.

An information processing method conducted in the information processing device 170 illustrated in FIG. 3 will be described with reference to FIG. 4. FIG. 4 is a flowchart illustrating an example of a processing procedure of an information processing method according to the first embodiment. Note that the respective processes illustrated in FIG. 4 may be executed by having the control unit 172 illustrated in FIG. 3 operate by following a certain program.

In the information processing method according to the first embodiment, first, detected values from the force sensor 150 are acquired by the control unit 172 (step S101). The detected values from the force sensor 150 may be provided directly to the acting force calculation unit 173 illustrated in FIG. 3, or temporarily stored in the storage unit 171.

Next, the acting forces on the forceps 110 at the first point of action and/or the second point of action are calculated by the acting force calculation unit 173, based on the acquired detected values (step S103). Specifically, the calculations described in (1-2. Acting force calculation method) above are performed by the acting force calculation unit 173, based on detected values from the force sensor 150 and various information stored in the storage unit 171, and the acting forces are calculated. Note that in the process illustrated in step S103, the acting forces may be calculated by using the results obtained by subtracting the component due to the gravitational force on the forceps 110 from the detected values from the first force sensor 150.

Finally, the calculation result by the acting force calculation unit 173 is output (step S105). The output destination of the calculation result is the control device of the support arm device that causes the forceps 110 to be driven, for example. In the control device, drive control of the arm unit 160 and control of force feedback into the operator's controller are conducted based on the calculation result.

The above thus describes an information processing method according to the first embodiment with reference to FIG. 4.

2. Second Embodiment

As discussed above, in the first embodiment, the acting forces on the forceps 110 at the first point of action and/or the second point of action are calculated, without accounting for active forces acting on the forceps 110. However, in actual practice, the detected values from the force sensor 150 include the influence from forces applied to the forceps 110 as a result of causing the motor 120 to drive. The second embodiment also accounts for active forces, and thereby calculates with higher precision the acting forces on the forceps 110 at the first point of action and/or the second point of action.

(2-1. Configuration of System)

Figure 5:
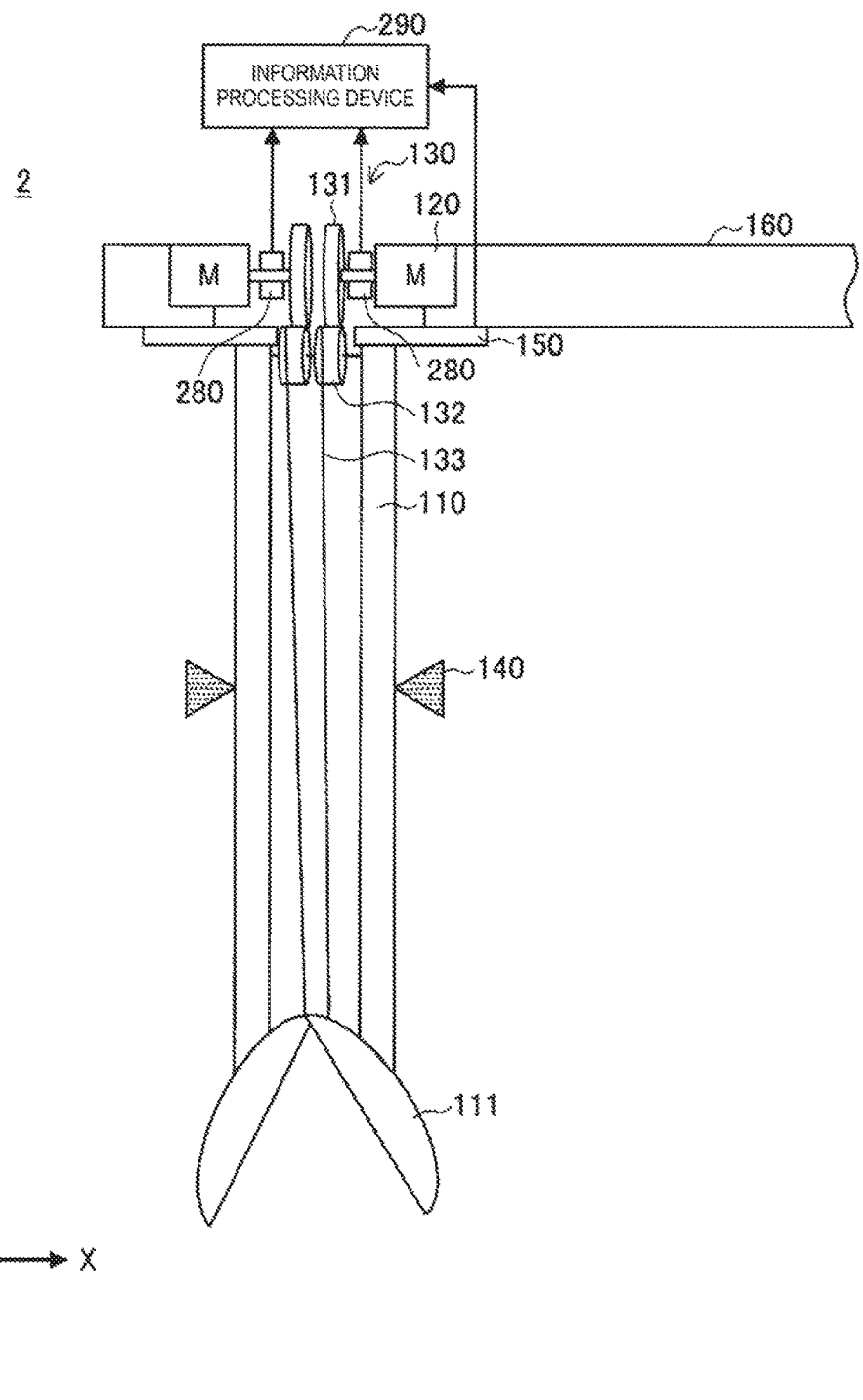
FIG. 5 is a diagram illustrating a diagrammatic configuration of a system according to a second embodiment of the present disclosure.

A diagrammatic configuration of a system according to the second embodiment of the present disclosure will be described with reference to FIG. 5. FIG. 5 is a diagram illustrating a diagrammatic configuration of a system according to the second embodiment of the present disclosure. Note that the system according to the second embodiment corresponds to the system 1 according to the first embodiment described with reference to FIG. 1, but with the addition of a force sensor 280 discussed later, and a corresponding modification to the functions of the information processing device 170. Since the configuration and function of other members are similar to the system 1, in the following description of the second embodiment, detailed description of items overlapping with the first embodiment will be reduced or omitted, and the differences from the first embodiment will be described primarily.

Referring to FIG. 5, the system 2 according to the second embodiment is equipped with the forceps 110, the motor 120, the transmission member 130, the trocar 140, force sensors 150 and 280, and an information processing device 290. Herein, the configuration and function of the forceps 110, the motor 120, the transmission member 130, the trocar 140, and the force sensor 150 are similar to the configuration and function of these members in the first embodiment, and thus detailed description will be omitted.

The force sensor 280 is provided on the drive shaft of the motor 120, and is a torque sensor that detects the torque of the drive shaft. Hereinafter, to distinguish between the force sensor 150 and the force sensor 280, the force sensor 150 will also be designated the first force sensor 150, and the force sensor 280 will also be designated the second force sensor 280. In the example illustrated in FIG. 5, the second force sensor 280 is provided respectively on the drive shafts of two motors 120. The second force sensor 280 and the information processing device 290 are communicably connected, and information about the torque of the drive shaft of the motor 120 detected by the second force sensor 280 is transmitted to the information processing device 290. The torque detection interval of the second force sensor 280 and the interval of transmitting information about detected values from the second force sensor 280 to the information processing device 290 are synchronized with the detection interval of the first force sensor 150 and the interval of transmitting information about detected values from the first force sensor 150 to the information processing device 290, for example. Since the detected values from the first force sensor 150 may change as a result of a change in the forces acting on the forceps 110, and the detected values from the second force sensor 280 may change as a result of a change in the driving force of the motor 120, by synchronizing the first force sensor 150 and the second force sensor 280 with each other and detecting the forces and moments (torques) at the same timings, more accurate detected values that also account for change over time may be obtained. Note that the method of communication between the second force sensor 280 and the information processing device 290 may be wired or wireless, and an arbitrary communication scheme may be applied thereto.

The information processing device 290 calculates the forces acting on the first point of action and/or the second point of action of the forceps 110, based on detected values from the first force sensor 150 and detected values from the second force sensor 280. The information processing device 290 may also calculate the acting forces on the forceps 110 continually on a certain interval, in accordance with the detection interval of the first force sensor 150 and the second force sensor 280. As discussed above, the detected value from the second force sensor 280 is the torque of the drive shaft of the motor 120, and expresses a force acting on the forceps 110 due to the motor 120 driving, or in other words, an active force. In the second embodiment, the information processing device 290 calculates the forces acting on the first point of action and/or the second point of action of the forceps 110 by using both the detected values from the first force sensor 150 and the detected values from the second force sensor 280 to remove the influence due to the active force. Consequently, higher-precision calculation that also accounts for active forces becomes possible. Note that details about the calculation process conducted by the information processing device 290 will be described further in (2-2. Acting force calculation method) and (2-3. Functional configuration) below.

Note that for the information processing device 290, similarly to the information processing device 170 according to the first embodiment, it is sufficient to operate according to a certain program and include a function of conducting the calculation process discussed above, whereas the specific configuration is not limited. For example, the information processing device 290 may be a device such as a PC, a server, or a processor.

The above thus describes a diagrammatic configuration of the system 2 according to the second embodiment with reference to FIG. 5.

(2-2. Acting Force Calculation Method)

Figure 6:
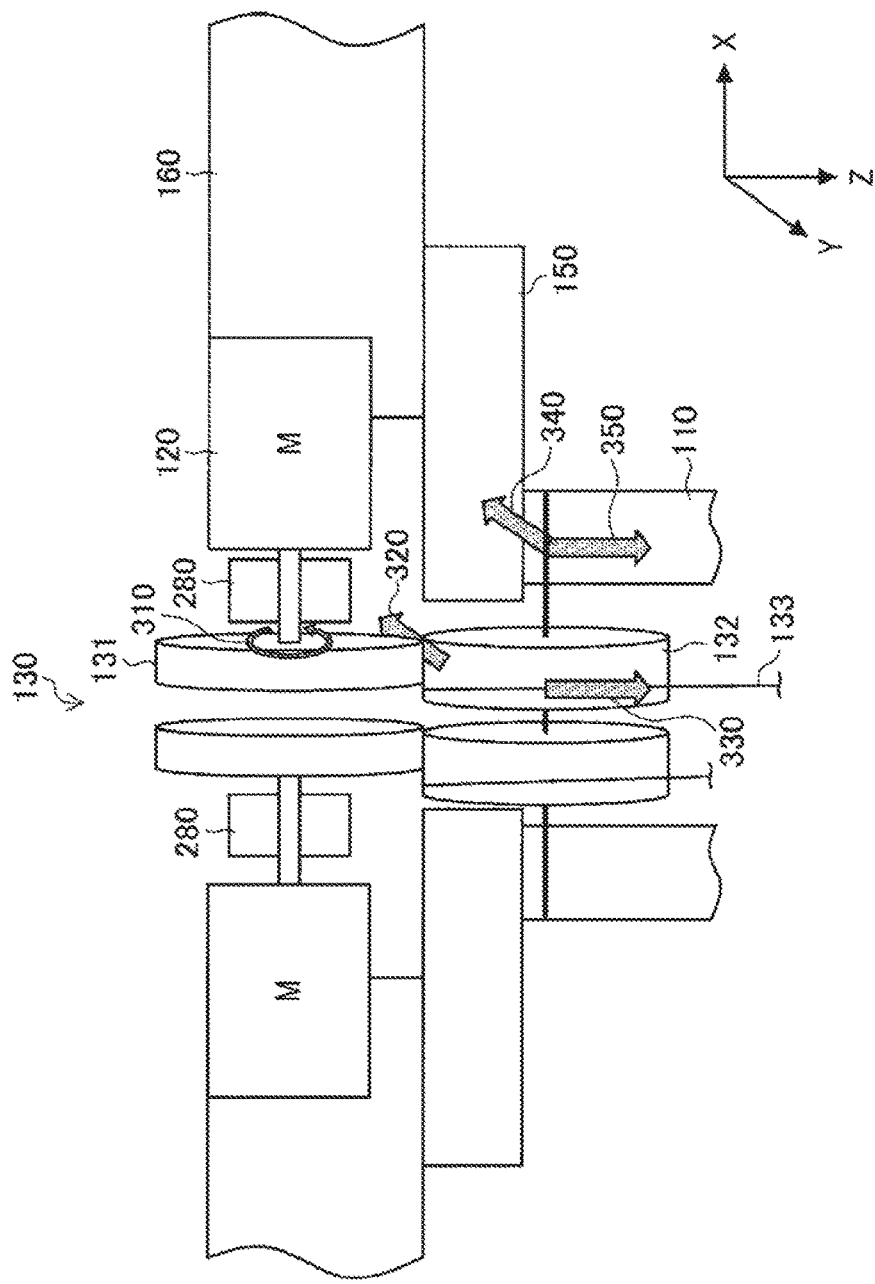
FIG. 6 is an explanatory diagram for explaining a method of calculating acting forces on a first point of action and/or a second point of action of forceps in a second embodiment.

A method of calculating the acting forces on the first point of action and/or the second point of action of the forceps 110 executed in the information processing device 290 discussed above will be described with reference to FIG. 6. FIG. 6 is an explanatory diagram for explaining a method of calculating acting forces on a first point of action and/or a second point of action of the forceps 110 in the second embodiment. Note that since FIG. 6 is an enlarged view of the area around the connecting section between the arm unit 160 and the forceps 110 in FIG. 5, duplicate description will be reduced or omitted for the configuration already described with reference to FIG. 5.

Herein, in the calculation method according to the second embodiment, the method of computing the forces and moments at the first point of action (Fx, Fy, Fz, Mx, My, and Mz discussed earlier) and the forces and moments at the second point of action (Ftx, Fty, Ftz, Mtx, Mty, and Mtz discussed earlier) based on the detected values from the first force sensor 150 (Fsx, Fsy, Fsz, Msx, Msy, and Msz discussed earlier) is similar to the first embodiment. In other words, likewise in the second embodiment, the above formulas (1) to (6) are established based on constraint conditions similar to the method described in (1-2. Acting force calculation method) above, and the unknown quantities, namely Fx, Fy, Fz, Mz, Ftx, and Fty are calculated using these formulas (1) to (6). However, in the second embodiment, the formulas (1) to (6) are solved by treating Fsx, Fsy, Fsz, Msx, Msy, and Msz as the results obtained after subtracting, from the detected values from the first force sensor 150, the component of the active forces computed from the detected values of the second force sensor 280. At this point, the active forces will be described with reference to FIG. 6.

In FIG. 6, the forces and moments (torques) that may act on components such as the forceps 110 and the transmission member 130 due to the motor 120 driving are illustrated by arrows.

The torque 310 represents the torque applied to the drive shaft due to the motor 120 driving. The second force sensor 280 is provided to detect the torque 310.

The force 320 represents the force that the gear 131 subjected to the torque 310 applies to the gear 132. The force 330 represents the force by which the gear 132 subjected to the force 320 pulls tight the wire 133 (tensile force). In other words, the force 330 may also be considered to be the force by which the wire 133 pulls tight the leading edge of the forceps 110.

Herein, although omitted from illustration in FIGS. 1 and 5, the gear 132 actually is configured so that its rotating shaft is axially supported by the forceps 110, as illustrated in FIG. 6. Consequently, the rotation of the gear 132 subjected to the force 320 may cause a force 340 to be applied to the forceps 110 via the rotating shaft. Also, the rotating shaft of the gear 132 subjected to the force 330, namely the tensile force of the wire 133, may also produce a force 350 applied to the forceps.

Of these forces and torques, the force 330, which is the tensile force produced in the wire 133, and the force 350, to which the forceps 110 is subjected by the force 33, exist in a mutually annihilating relationship. Consequently, while the motor 120 is driving and the forceps 110 is moving, on the forceps 110, besides the forces acting on the first point of action and the second point of action, the force 340 may be detected by the first force sensor 150. In this way, the force 340 may become noise when calculating the acting forces at the first point of action and the second point of action from the detected values from the first force sensor 150.

Meanwhile, the force 340 is the force produced due to the torque 310 being transmitted via the gears 131 and 132, and may be computed easily based on the shapes of the gears 131 and 132, and the value of the torque 310. Accordingly, in the second embodiment, the information processing device 290 conducts a process of calculating the forces and moment imparted to the forceps 110 according to the driving force of the motor 120 (in other words, the force 340 and the moment caused by the force 340) based on the detected values from the second force sensor 280 (in other words, the torque 310), and subtracts the component of the calculated force 340 from the detected values from the first force sensor 150. Subsequently, the information processing device 290 uses the detected values from the force sensor 150 from which the component of the force 340 has been removed (in other words, treats the detected values from the force sensor 150 from which the component of the force 340 has been removed as Fsx, Fsy, Fsz, Msx, Msy, and Msz), and calculates the acting forces at the first point of action and/or the second point of action according to a method similar to the method described in (1-2. Acting force calculation method) above. By conducting such a process, it becomes possible to perform a more high-precision calculation of the acting forces at the first point of action and the second point of action, with the influence due to active forces removed.

Note that FIG. 6 illustrates the forces and moments due to the driving force from one of the two motors 120, but likewise for the other motor 120, there exist forces and moments (torques) that may act on components such as the forceps 110 and the transmission member 130 due to the other motor 120 driving. In the second embodiment, the second force sensor 280 is also provided on the drive shaft of the other motor 120. Also, the information processing device 290 additionally uses the detected values from the other second force sensor 280 to calculate the forces and moments imparted to the forceps 110 according to the driving forces of both motors 120, removes the influence of the driving forces of both motors 120, and calculates the acting forces at the first point of action and/or the second point of action.

The above thus describes a method of calculating the acting forces according to the second embodiment.

(2-3. Functional Configuration)

Figure 7:
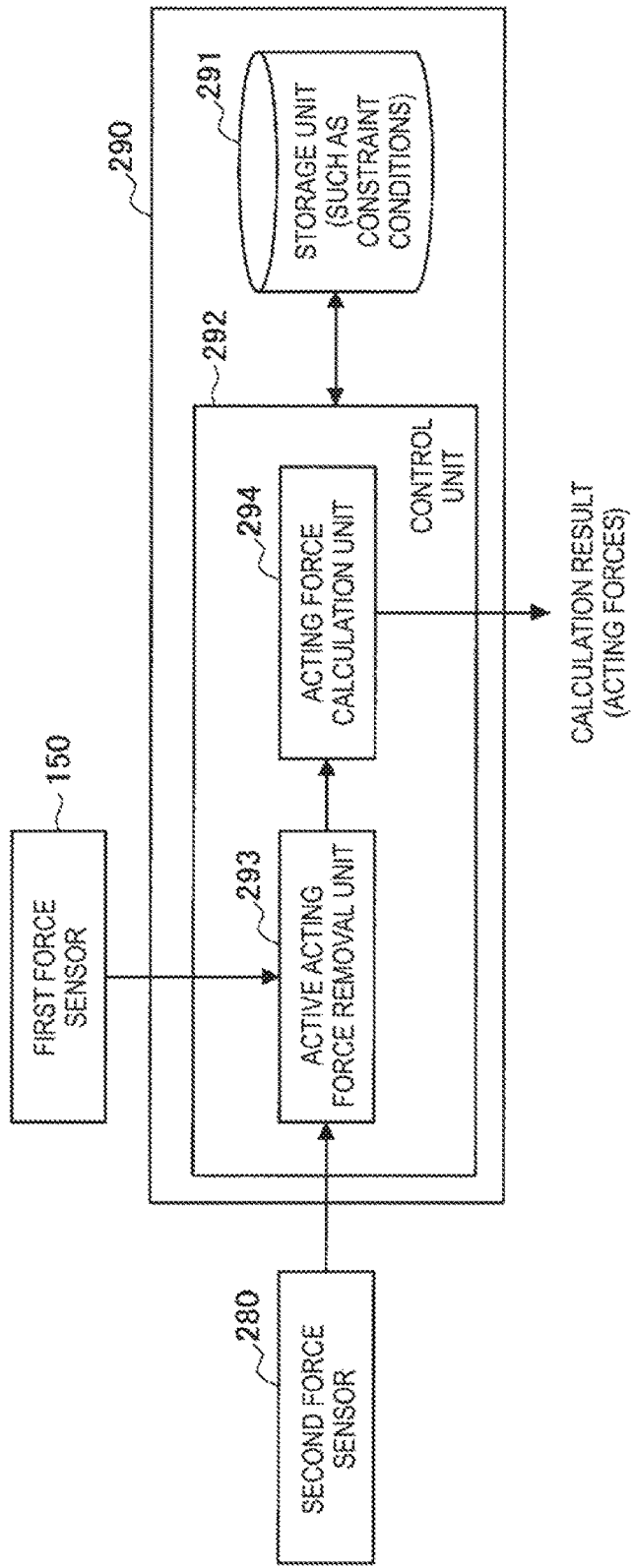
FIG. 7 is a block diagram illustrating a functional configuration of an information processing device according to a second embodiment.

Next, a functional configuration of the information processing device 290 that executes the calculation described above will be described with reference to FIG. 7. FIG. 7 is a block diagram illustrating a functional configuration of the information processing device 290 according to the second embodiment.

Referring to FIG. 7, the information processing device 290 according to the second embodiment is equipped with a storage unit 291 and a control unit 292. As illustrated, the information processing device 290 is connected to the first force sensor 150 and the second force sensor 280, enabling the communication of various types of information. Note that in FIG. 7, the second force sensor 280 is illustrated schematically as a single block, but in actuality, the second force sensor 280 is provided for each of the motors 120 as illustrated in FIG. 5, and the detected values from these multiple second force sensors 280 are transmitted to the information processing device 290. The information processing device 290 is able to acquire from the first force sensor 150 information about the detected values detected by the first force sensor 150 (in other words, forces and moment), and also acquire from the second force sensor 280 information about the detected values detected by the second force sensor 280 (in other words, the torque acting on the drive shaft of the motor 120). Also, although omitted from illustration, the information processing device 290 is also connected to the control device that controls the driving of the arm unit 160, enabling the communication of various types of information. The information processing device 290 is able to acquire, from the control device, information such as information about the positions and the orientations of the arm unit 160 and the forceps 110, and information necessary to calculate Lt and Ls discussed above.

The storage unit 291 is made up of any of various types of storage devices, such as a magnetic storage device like an HDD, a semiconductor storage device, an optical storage device, or a magneto-optical storage device, for example, and stores various information processed by the control unit 292 and the results of processes by the control unit 292. The control unit 292 is able to execute various processes by utilizing the various information stored in the storage unit 291.

The storage unit 291 stores similar information as the storage unit 171 according to the first embodiment. However, in the second embodiment, the storage unit 291 is able to store, in addition to this information, detected values from the second force sensor 280. Furthermore, the storage unit 291 stores various information required to compute, from the detected values from the second force sensor 280, the component of the force 340 illustrated in FIG. 6 which is included in the detected values from the first force sensor 150 (for example, information about the shapes, installation positions, and the like of the gears 131 and 132). This information may be determined according to the configuration of the arm unit 160 and the forceps 110, and thus may be input into the storage unit 171 in advance by a person such as the operator or a designer of the system 1, prior to surgery.

The control unit 292 is made up of any of various types of processors, such as a CPU or a DSP, for example, and centrally controls various processes in the information processing device 290. The control unit 292 includes an active acting force removal unit 293 and an acting force calculation unit 294 as functions. Note that the respective functions of the control unit 292 may be realized by having any of various types of processors constituting the control unit 292 operate by following a certain program.

Information about detected values is input from the first force sensor 150 and the second force sensor 280 into the active acting force removal unit 293. From the detected values from the second force sensor 280, the active acting force removal unit 293 calculates the component of the forces and moments applied to the forceps 110 due to the driving force of the motor 120 which is included in the detected values from the first force sensor 150 (in other words, the force 340 and moment caused by the force 340 illustrated in FIG. 6). For this calculation, information about the shapes, installation positions, and the like of the gears 131 and 132 stored in the storage unit 291 may be used. The active acting force removal unit 293 conducts a process of subtracting the component caused by the driving force of the motor 120 from the detected values from the first force sensor 150, based on the calculation result. The active acting force removal unit 293 provides the acting force calculation unit 294 with the value obtained by subtracting the component caused by the driving force of the motor 120 from the detected values from the first force sensor 150 (in other words, the value obtained by subtracting the component due to the active forces from the detected values from the first force sensor 150). Note that the detected values from the first force sensor 150 and the second force sensor 280 may also be stored in the storage unit 291 temporarily after being transmitted to the information processing device 290, and the active acting force removal unit 293 may obtain detected values from the first force sensor 150 and the second force sensor 280 to use in the calculations by referencing the storage unit 291.

Note that, as illustrated in FIG. 5, in a case in which multiple second force sensors 280 are provided in correspondence with multiple motors 120, the active acting force removal unit 293 may calculate combined values of the forces and moments applied to the forceps 110 by the driving forces of the multiple motors 120, based on the detected values from each of these multiple second force sensors 280, and subtract the combined values from the detected values from the first force sensor 150.

The acting force calculation unit 294 calculates the acting forces on the first point of action and/or the second point of action of the forceps 110, based on detected values from the first force sensor 150 and detected values from the second force sensor 280. Specifically, the acting force calculation unit 294 performs the calculations described in (1-2. Acting force calculation method) above, based on detected values from the first force sensor 150 and various information stored in the storage unit 171, and calculates the acting forces on the forceps 110. However, in the calculation process, the acting force calculation unit 294 uses the values provided by the active acting force removal unit 293, in which the component due to active forces has been subtracted from the detected values from the first force sensor 150, as $F_{sx}$, $F_{sy}$, $F_{sz}$, $M_{sx}$, $M_{sy}$, and $M_{sz}$ in the above formulas (1) to (12). Note that $F_{sx}$, $F_{sy}$, $F_{sz}$, $M_{sx}$, $M_{sy}$, and $M_{sz}$ may be the values obtained by subtracting the component due to active forces from the detected values from the first force sensor 150, and also by additionally subtracting the component due to the gravitational force on the forceps 110, similarly to the first embodiment. Other than using values obtained by subtracting the component due to active forces from the detected values from the first force sensor 150 as $F_{sx}$, $F_{sy}$, $F_{sz}$, $M_{sx}$, $M_{sy}$, and $M_{sz}$, the functions of the acting force calculation unit 294 are mostly similar to the functions of the acting force calculation unit 173 according to the first embodiment, and thus herein, detailed description of the other functions of the acting force calculation unit 294 is omitted.

The acting forces on the forceps 110 calculated by the acting force calculation unit 294 are transmitted to the above control device, for example. In the control device, control of the arm unit 160 and control of force feedback into the operator's controller are conducted based on the calculated acting forces on the forceps 110. Alternatively, calculation results by the acting force calculation unit 294 may be displayed on a display unit (not illustrated) or transmitted to other equipment via a communication unit (not illustrated), and output to the operator or the like in a format such as numerical values or graphs.

The above thus describes a functional configuration of the information processing device 290 with reference to FIG. 7. According to the second embodiment, in addition to the advantageous effects obtained by the first embodiment discussed earlier, the following advantageous effects may be obtained. Namely, according to the second embodiment, the torque of the drive shaft of the motor 120 is detected by the second force sensor 280. Subsequently, based on detected values from the second force sensor 280, the acting forces on the first point of action and/or the second point of action of the forceps 110, from which the influence of the driving force of the motor 120 has been removed, are calculated. Consequently, even if the motor 120 is driving and the forceps 110 is currently moving, the forces acting on the forceps 110 may be detected more accurately.

Note that in FIG. 7, for the sake of simplicity, only the functions characteristic of the second embodiment are illustrated, while other functions are omitted from illustration. The information processing device 290, similarly to the information processing device 170 according to the first embodiment, additionally may be provided with any of various functions included in a typical information processing device, such as an input unit, an output unit, and a communication unit.

In addition, the device configuration of the information processing device 290 is not limited to the example illustrated in FIG. 7. For example, the respective functions of the information processing device 290 illustrated in FIG. 7 may not necessarily be provided onboard a single device in an integrated manner. The respective functions provided onboard the information processing device 290 illustrated in FIG. 7 may also be provided onboard multiple devices in a distributed manner, and the information processing device 290 may be configured by communicably connecting these multiple devices. For example, the storage unit 291 may also be provided as external equipment different from the information processing device 290, and the information processing device 290 may execute the calculation process discussed above while communicating with the external equipment, namely the storage unit 291. Also, the respective functions of the control unit 292 illustrated in the drawing may also be executed by mutually different devices. For example, the respective functions of the control unit 292 may be executed by a single processor, or may be executed by the cooperative action of multiple processors.

Additionally, it is possible to develop a computer program for realizing the functions of the information processing device 290 according to the second embodiment as discussed above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

(2-4. Information Processing Method)

Figure 8:
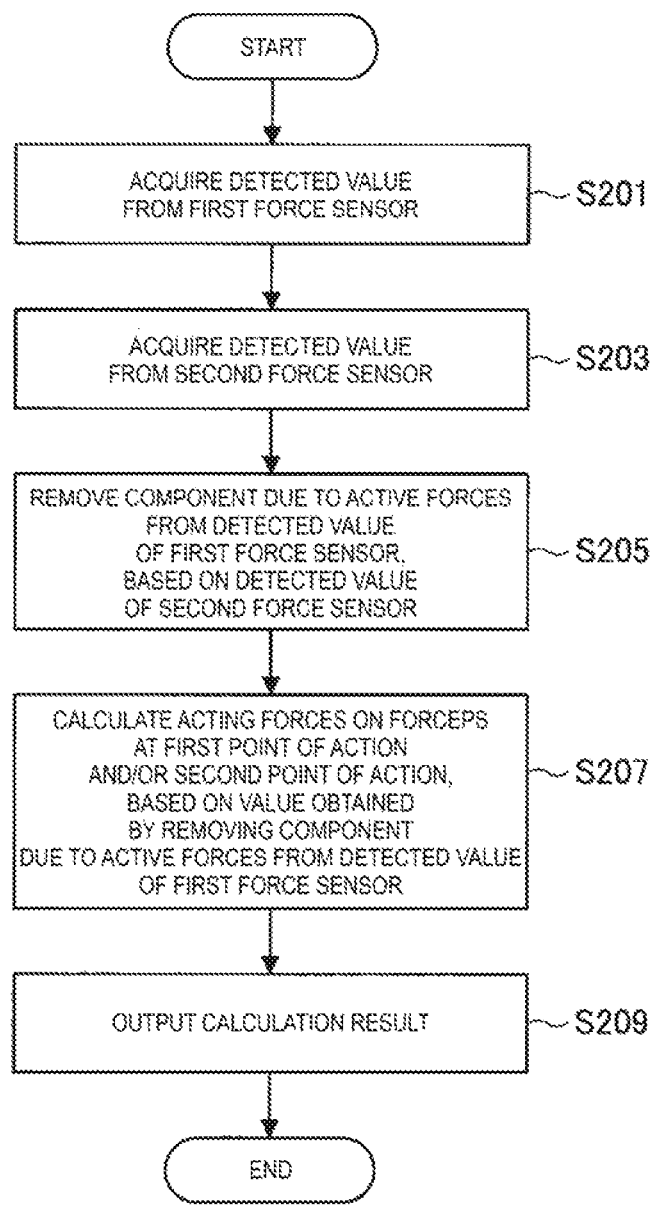
FIG. 8 is a flowchart illustrating an example of a processing procedure of an information processing method according to a second embodiment.

An information processing method conducted in the information processing device 290 illustrated in FIG. 7 will be described with reference to FIG. 8. FIG. 8 is a flowchart illustrating an example of a processing procedure of an information processing method according to the second embodiment. Note that the respective processes illustrated in FIG. 8 may be executed by having the control unit 292 illustrated in FIG. 7 operate by following a certain program.

In the information processing method according to the second embodiment, first, detected values from the first force sensor 150 are acquired by the control unit 292 (step S201). Next, detected values from the second force sensor 280 are acquired by the control unit 292 (step S203). Note that in FIG. 8, the process indicated in step S201 and the process indicated in step S203 are illustrated as being executed sequentially for the sake of convenience, but in actuality, these processes may be conducted at the same time. Also, detected values from the first force sensor 150 and the second force sensor 280 may be provided directly to the active acting force removal unit 293 illustrated in FIG. 7, or temporarily stored in the storage unit 291.

Next, based on the detected values from the second force sensor 280, the component due to active forces is removed from the detected values from the first force sensor 150 by the active acting force removal unit 293 (step S205). Specifically, based on the detected values from the second force sensor 280 and information such as the shapes of the gears 131 and 132 stored in the storage unit 291, the active forces, that is, the forces and moments applied to the forceps 110 by the driving force of the motor 120, are calculated by the active acting force removal unit 293. Subsequently, the component corresponding to the calculation result is subtracted from the detected values from the first force sensor 150 by the active acting force removal unit 293.

Next, based on the values obtained by subtracting the component due to active forces from the detected values from the first force sensor 150, the acting forces on the forceps at the first point of action and/or the second point of action are calculated by the acting force calculation unit 294 (step S207). Specifically, the calculations described in (1-2. Acting force calculation method) above are performed by the acting force calculation unit 294, based on the values calculated in step S205 (the values obtained by subtracting the component due to active forces from the detected values from the first force sensor 150) and various information stored in the storage unit 291, and the acting forces are calculated. Note that in the process illustrated in step S207, the acting forces may be calculated by using the results obtained by additionally subtracting the component due to the gravitational force on the forceps 110 from the values obtained by subtracting the component due to active forces from the detected values from the first force sensor 150.

Finally, the calculation result by the acting force calculation unit 294 is output (step S209). The output destination of the calculation result is the control device of the support arm device that causes the forceps 110 to be driven, for example. In the control device, drive control of the arm unit 160 and control of force feedback into the operator's controller are conducted based on the calculation result.

The above thus describes an information processing method according to the second embodiment with reference to FIG. 8.

3. Modifications

Modifications of the first embodiment and the second embodiment described above will now be described.

(3-1. Modification of First Embodiment)

Figure 9:
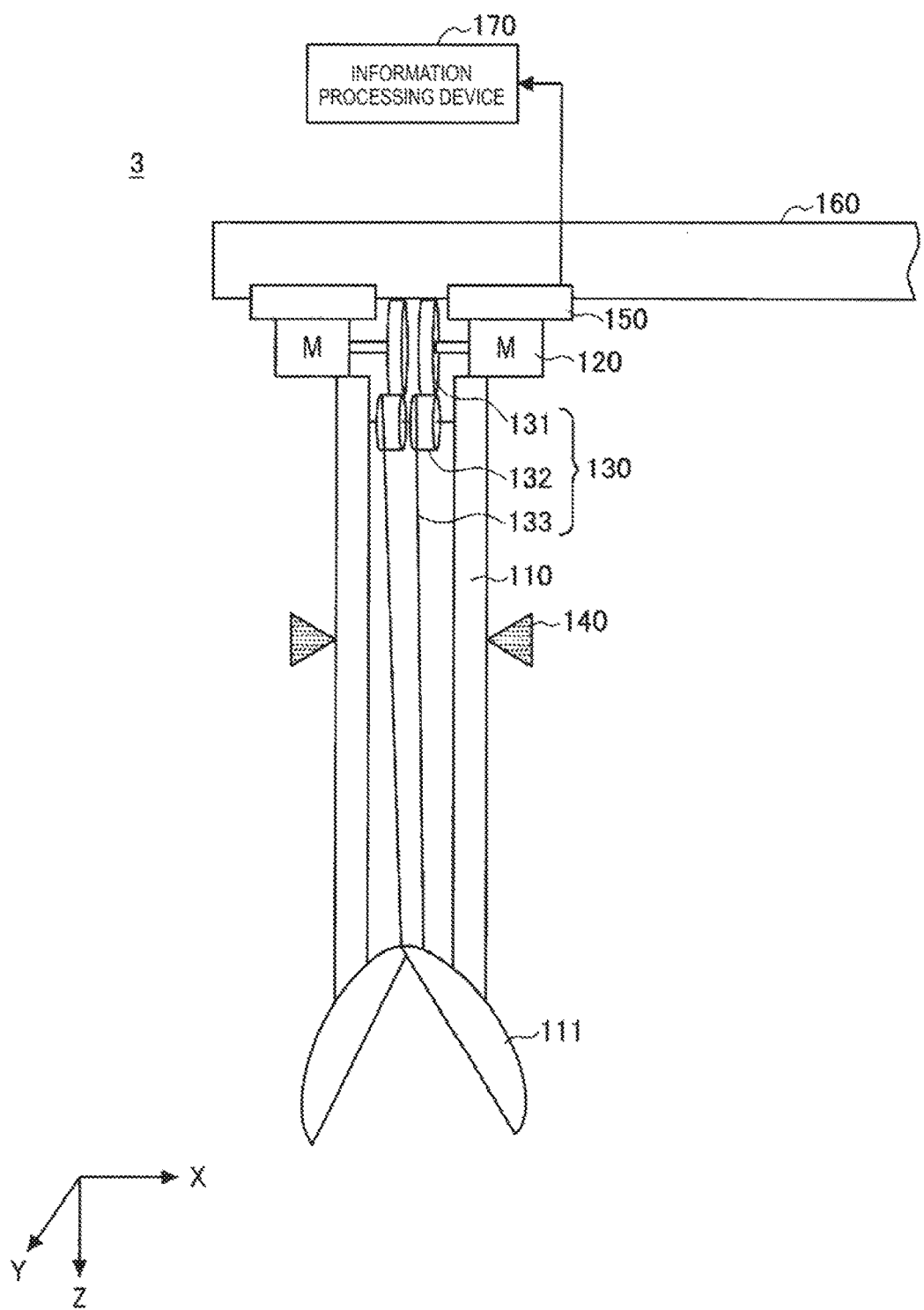
FIG. 9 is a diagram illustrating a diagrammatic configuration of a system according to a modification of a first embodiment in which the disposed position of a force sensor has been changed.

A modification of the first embodiment in which the disposed position of the force sensor 150 has been changed will be described with reference to FIG. 9. FIG. 9 is a diagram illustrating a diagrammatic configuration of a system according to a modification of the first embodiment in which the disposed position of the force sensor 150 has been changed. Note that the system according to the present modification corresponds to the system 1 according to the first embodiment described with reference to FIG. 1, but in which the disposed position of the force sensor 150 has been changed, while the configuration and function of other members are similar to the system 1. Consequently, in the following description of the present modification, detailed description of items overlapping with the first embodiment will be reduced or omitted, and the differences from the first embodiment will be described primarily.

Referring to FIG. 5, the system 3 according to the present modification is equipped with the forceps 110, the motor 120, the transmission member 130, the trocar 140, the force sensor 150, and the information processing device 170. Herein, the configuration and function of the forceps 110, the motor 120, the transmission member 130, the trocar 140, the force sensor 150, and the information processing device 170 are similar to the configuration and function of these members in the first embodiment, and thus detailed description will be omitted.

As illustrated in FIG. 9, in the system 3 according to the present modification, the force sensor 150 is provided preceding the motor 120. In other words, the force sensor 150 is attached directly to the arm unit 160, and the force sensor 150 is connected to the forceps 110 via the motor 120. Even with such a configuration, it is possible to calculate the acting forces on the forceps 110 at the first point of action and/or the second point of action based on the detected values from the force sensor 150, according to a method similar to the first embodiment.

However, in the first embodiment discussed earlier, the force sensor 150 is attached to the connecting section between the forceps 110 and the arm unit 160 so as to support the forceps 110 (see FIG. 1). Consequently, when conducting the process of subtracting the component due to the weight of the forceps 110 itself from the detected values from the force sensor 150, it is sufficient to account for the mass, position, and orientation of the forceps 110. On the other hand, as illustrated in FIG. 9, in the present modification, not only the gravitational force acting on the forceps 110, but also the gravitational force acting on the motor 120 and the transmission member 130 may be detected by the force sensor 150. Consequently, in the present modification, the information processing device 170 may conduct a process of subtracting the components due to the gravitational forces acting on the forceps 110, the motor 120, and the transmission member 130 from the detected values from the force sensor 150, treat the values from which these components are subtracted as Fsx, Fsy, Fsz, Msx, Msy, and Msz, and conduct the process of solving the above formulas (1) to (6).

The above thus describes a modification of the first embodiment in which the disposed position of the force sensor 150 has been changed with reference to FIG. 9. Note that, regarding the disposed position of the force sensor 150, whether to take a configuration like the system 1 illustrated in FIG. 1 or to take a configuration like the system 3 illustrated in FIG. 9 may be decided appropriately to enable easier installation of the force sensor 150, according to factors such as the structure of the arm unit 160 and the structure of the connecting section between the arm unit 160 and the forceps 110.

(3-2. Modification of Second Embodiment)

Figure 10:
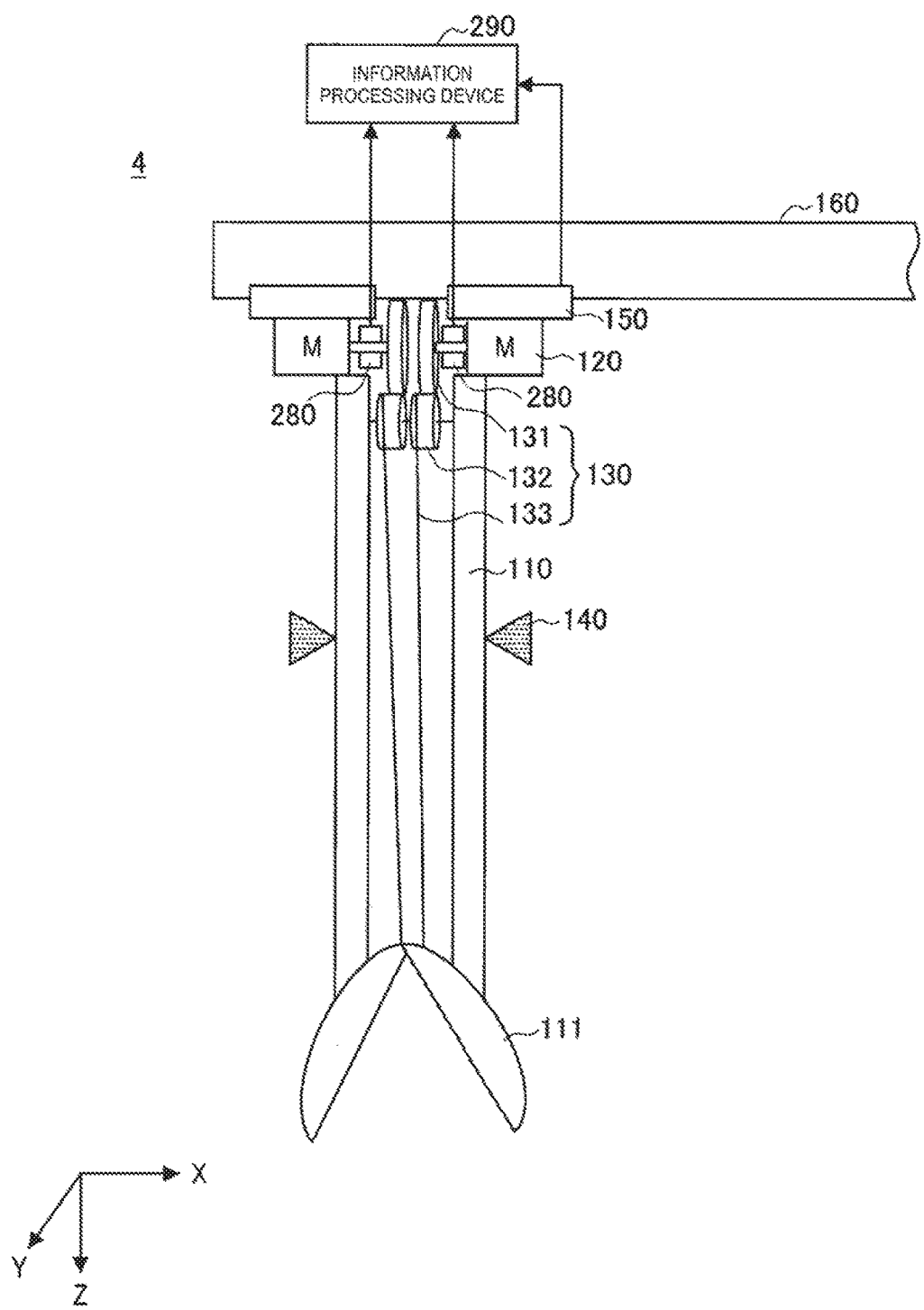
FIG. 10 is a diagram illustrating a diagrammatic configuration of a system according to a modification of a second embodiment in which the disposed position of a first force sensor has been changed.

A modification of the second embodiment in which the disposed position of the first force sensor 150 has been changed will be described with reference to FIG. 10. FIG. 10 is a diagram illustrating a diagrammatic configuration of a system according to a modification of the second embodiment in which the disposed position of the first force sensor 150 has been changed. Note that the system according to the present modification corresponds to the system 2 according to the second embodiment described with reference to FIG. 5, but in which the disposed position of the first force sensor 150 has been changed, while the configuration and function of other members are similar to the system 2. Consequently, in the following description of the present modification, detailed description of items overlapping with the second embodiment will be reduced or omitted, and the differences from the second embodiment will be described primarily.

Referring to FIG. 10, the system 4 according to the present modification is equipped with the forceps 110, the motor 120, the transmission member 130, the trocar 140, the first force sensor 150, the second force sensor 280, and the information processing device 290. Herein, the configuration and function of the forceps 110, the motor 120, the transmission member 130, the trocar 140, the first force sensor 150, the second force sensor 280, and the information processing device 290 are similar to the configuration and function of these members in the second embodiment, and thus detailed description will be omitted.

As illustrated in FIG. 10, in the system 4 according to the present modification, the first force sensor 150 is provided preceding the motor 120. In other words, the first force sensor 150 is attached directly to the arm unit 160, and the first force sensor 150 is connected to the forceps 110 via the motor 120. Even with such a configuration, it is possible to calculate the acting forces on the forceps at the first point of action and the second point of action based on the detected values from the first force sensor 150 and the second force sensor 280, according to a method similar to the second embodiment.

However, similarly to the system 3 described in (3-1. Modification of first embodiment) above, in the present modification, not only the gravitational force acting on the forceps 110, but also the gravitational force acting on the motor 120 and the transmission member 130 may be detected by the first force sensor 150. Consequently, in the present modification, the information processing device 290 conducts a process of subtracting the components due to the gravitational forces acting on the forceps 110, the motor 120, and the transmission member 130 from the detected values from the first force sensor 150, treats the values from which these components are subtracted as Fsx, Fsy, Fsz, Msx, Msy, and Msz, and conducts the process of solving the above formulas (1) to (6).

The above thus describes a modification of the second embodiment in which the disposed position of the force sensor 150 has been changed with reference to FIG. 10. Note that, regarding the disposed position of the force sensor 150, whether to take a configuration like the system 2 illustrated in FIG. 5 or to take a configuration like the system 4 illustrated in FIG. 10 may be decided appropriately to enable easier installation of the force sensor 150, according to factors such as the structure of the arm unit 160 and the structure of the connecting section between the arm unit 160 and the forceps 110.

(3-3. Modification in which Six-Axis Force Sensor is Used Instead of Torque Sensor)

In the second embodiment discussed above, a torque sensor is used as the second force sensor 280, and based on the detected values from the torque sensor, the process of removing the influence due to active forces from the detected values from the first force sensor 150 is conducted. However, the second embodiment is not limited to such an example, and another type of force sensor, such as a six-axis force sensor, for example, may also be used as the second force sensor 280. Even if a six-axis force sensor is used as the second force sensor 280, it is still possible to remove the influence due to active forces similarly.

In the case in which a six-axis force sensor is used as the second force sensor 280, the six-axis force sensor is attached directly to the motor 120 illustrated in FIG. 1, for example. According to this configuration, the forces and moments detected by the force sensor 150 include a component due to the acting forces on the forceps 110 at the first point of action, a component due to the acting forces on the forceps 110 at the second point of action, a component due to the gravitational force corresponding to the weight of the forceps 110 itself, and a component due to the driving force of the motor 120. On the other hand, the forces and moment acting on the forceps 110 and detected by the second force sensor 280 which is a six-axis sensor include a component due to the gravitational force corresponding to the weight of the motor 120 itself, and a component due to the driving force of the motor 120.

Since the mass of the forceps 110 and the mass of the motor 120 are known, among the respective components above, the component due to the gravitational force corresponding to the weight of the forceps 110 itself and the component due to the gravitational force corresponding to the weight of the motor 120 itself are calculable. Consequently, according to the present modification, by computing the component due to the driving force of the motor 120 based on the detected values from the second force sensor 280, and subtracting the computed result from the detected values from the first force sensor 150, it becomes possible to compute the forces acting on the first point of action and/or the second point of action of the forceps 110 from which the influence due to active forces has been removed.

Note that whereas the component due to the driving force of the motor 120 included in the detected values from the second force sensor 280 is detected by the second force sensor 280 attached directly to the motor 120, the component due to the driving force of the motor 120 included in the detected values from the first force sensor 150 is detected via the transmission member 130, and thus the relationship between the two may vary depending on the position and the orientation of the forceps 110. Consequently, in the present modification, variation in the detected values from the first force sensor 150 and the detected values from the second force sensor 280 corresponding to the position and the orientation of the forceps 110 may be learned in advance, and the above process of removing the influence due to active forces may be executed on the basis of the learned content.

4. Hardware Configuration

Figure 11:
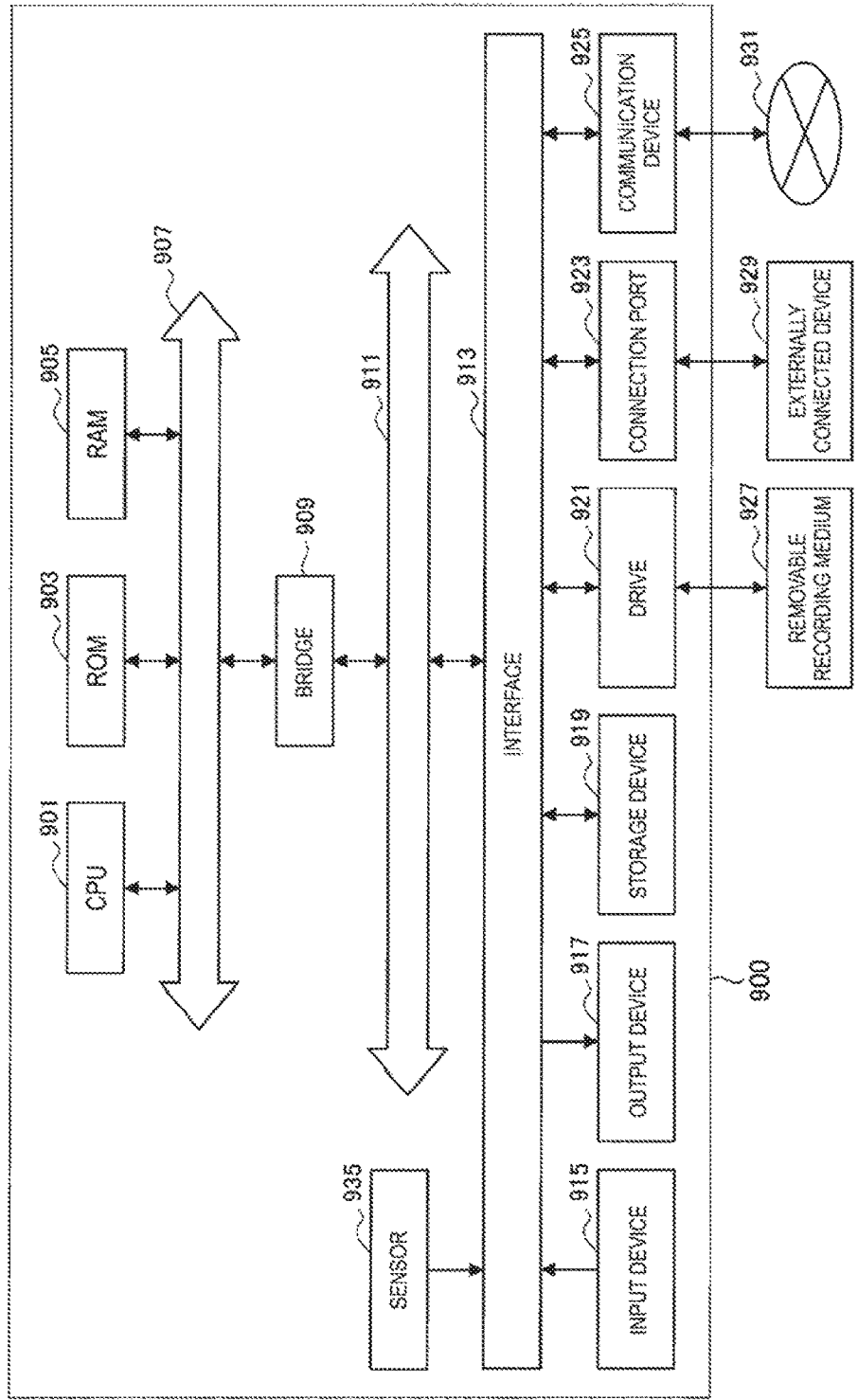
FIG. 11 is a function block diagram illustrating an example of a hardware configuration of a system according to first and second embodiments.

Next, a hardware configuration of a system according to the first and second embodiments will be described with reference to FIG. 11. FIG. 11 is a function block diagram illustrating an example of a hardware configuration of a system according to the first and second embodiments. Note that the system 900 illustrated in FIG. 11 may realize any of the systems 1, 2, 3, and 4 illustrated in FIGS. 1, 5, 9, and 10, for example. Note that, although omitted from illustration in FIG. 11, the system 900 is equipped with a configuration corresponding to the forceps 110, the motor 120, the transmission member 130, the trocar 140, and the arm unit 160 illustrated in FIGS. 1, 5, 9, and 10.

The system 900 is equipped with a CPU 901, read-only memory (ROM) 903, and random access memory (RAM) 905. The system 900 may also be equipped with a host bus 907, a bridge 909, an external bus 911, an interface 913, an input device 915, an output device 917, a storage device 919, a drive 921, a connection port 923, a communication device 925, and a sensor 935. The system 900 may also include a processing circuit called a DSP or an application-specific integrated circuit (ASIC) instead of, or together with, the CPU 901.

The CPU 901 functions as a computational processing device and a control device, and controls all or part of the operation in the system 900 by following various programs recorded in the ROM 903, the RAM 905, the storage device 919, or a removable recording medium 927. The ROM 903 stores information such as programs and computational parameters used by the CPU 901. The RAM 905 primarily stores information such as programs used during execution by the CPU 901, and run-time parameters. The CPU 901 corresponds to the control unit 172 or 292 in the first and second embodiments discussed earlier, for example.

The CPU 901, the ROM 903, and the RAM 905 are connected to each other by a host bus 907 realized by an internal bus such as a CPU bus. Additionally, the host bus 907 is connected to an external bus 911 such as a Peripheral Component Interconnect/Interface (PCI) bus via the bridge 909.

The host bus 907 is connected to an external bus 911 such as a Peripheral Component Interconnect/Interface (PCI) bus via the bridge 909.

The input device 915 is made up of a device operated by a user, such as a mouse, a keyboard, a touch panel, or one or more buttons, switches, and levers, for example. In addition, the input device 915 may also be a remote control device utilizing infrared or some other electromagnetic wave (also referred to as a remote), and may also be an externally connected device 929 such as a mobile phone or PDA supporting the operation of the server 900, for example. Furthermore, the input device 915 is made up of an input control circuit or the like, which generates an input signal on the basis of information input by a user using the above operating means, and outputs the generated input signal to the CPU 901, for example. By operating the input device 915, a user of the system 900 is able to input various data and instruct the system 900 to perform processing operations, for example. In the first and second embodiments, information about constraint conditions or the like, and various information used to compute the acting forces on the first point of action and/or the second point of action of the forceps 110, for example, is input via the input device 915 by persons such as the operator and a designer of the system 900.

The output device 917 is realized by a device capable of visually or aurally reporting acquired information to a user. Such a device may be a display device such as a CRT display device, a liquid crystal display device, a plasma display device, an EL display device, or indicator lights, an audio output device such as one or more speakers and headphones, a printer, or the like. The output device 917 outputs results obtained by various processes conducted by the system 900, for example. Specifically, a display device visually displays results obtained by various processes conducted by the system 900 in various formats, such as text, images, tables, and graphs. In the first and second embodiments, calculation results of the acting forces on the first point of action and/or the second point of action of the forceps 110 are displayed on the display device, for example. On the other hand, an audio output device aurally outputs an analog signal converted from an audio signal made up of played-back speech data, sound data, or the like.

The storage device 919 is a device used for data storage, realized as an example of a storage unit in the system 900. The storage device 919 may be a magnetic storage device such as an HDD, a semiconductor storage device, an optical storage device, or a magneto-optical storage device, for example. The storage device 919 stores information such as programs executed by the CPU 901, various data, and various externally acquired data. The storage device 919 corresponds to the storage unit 171 or 291 in the first and second embodiments discussed earlier, for example. In the first and second embodiments, information about constraint conditions or the like, and various information used to compute the acting forces on the first point of action and/or the second point of action of the forceps 110, for example, is stored in the storage device 919.

The drive 921 is a reader/writer for a recording medium, and is internally housed inside, or externally attached to, the system 900. The drive 921 reads out information recorded onto a removable recording medium 927 such as an inserted magnetic disk, optical disc, magneto-optical disc, or semiconductor memory, and outputs such information to the RAM 905. In addition, the drive 921 is also capable of writing information onto a removable recording medium 927 such as an inserted magnetic disk, optical disc, magneto-optical disc, or semiconductor memory. The removable recording medium 927 is an instance of DVD media, HD-DVD media, or Blu-ray (registered trademark) media, for example. The removable recording medium 927 may also be a medium such as a CompactFlash (CF; registered trademark), flash memory, or Secure Digital (SD) memory card. Also, the removable recording medium 927 may be an integrated circuit (IC) card mounted with a contactless IC chip, or some other electronic equipment, for example. In the first and second embodiments, various information processed by the control unit 172 or 292, and various information stored in the storage unit 171 or 291, for example, may be read out from the removable recording medium 927 or written to the removable recording medium 927 by the drive 921.

The connection port 923 is a port for connecting equipment directly to the system 900. The connection port 923 may be a Universal Serial Bus (USB) port, an IEEE 1394 port, or a Small Computer System Interface (SCSI) port, for example. Other examples of the connection port 923 include an RS-232C port, an optical audio socket, or a High-Definition Multimedia Interface (HDMI (registered trademark)) port. By connecting an externally connected device 929 to the connection port 923, the system 900 is able to acquire various data from the externally connected device 929 directly, and provide various data to the externally connected device 929. In the first and second embodiments, various information processed by the control unit 172 or 292, and various information stored in the storage unit 171 or 291, for example, may be acquired from the externally connected device 929 or output to the externally connected device 929 via the connection port 923.

The communication device 925 is a communication interface realized by a communication device that connects to a communication network 931, for example. The communication device 925 is a device such as a wired or wireless local area network (LAN), Bluetooth (registered trademark), or Wireless USB (WUSB) communication card, for example. The communication device 925 may also be an optical communication router, an asymmetric digital subscriber line (ADSL) router, or a modem for any of various types of communication. The communication device 925 is able to transmit and receive signals or other information to and from the Internet or another communication device in accordance with a given protocol such as TCP/IP, for example. Also, the network 931 connected to the communication device 925 may be realized by a network or the like connected in a wired or wireless manner, and may be the Internet, a home LAN, infrared communication, radio-wave communication, or satellite communication, for example. In the first and second embodiments, communication between the information processing device 170 or 290 and the control device that controls the driving of the support arm device may be executed by the communication device 925 via the network 931, for example.

The sensor 935 is any of various sensors such as an acceleration sensor, a gyro sensor, a geomagnetic sensor, an optical sensor, a sound sensor, a range finding sensor, or a force sensor, for example. The sensor 935 acquires information related to the state of a member to which the sensor 935 is attached (such as the forceps 110 illustrated in FIGS. 1, 5, 9, and 10, for example), such as the orientation, the movement speed, or the acting forces on the member, for example, and also acquires information related to the surrounding environment around the member, such as the brightness and noise of the area around the member. The sensor 935 may also include a GPS sensor that receives GPS signals and measures the latitude, longitude, and altitude of the device. The sensor 935 corresponds to the first force sensor 150 and the second force sensor 280 in the first and second embodiments discussed earlier, for example.

The above thus illustrates an example of a hardware configuration able to realize the functions of the system 900 according to the present disclosure. Each of the above structural elements may be realized using general-purpose members, but may also be realized in hardware specialized in the function of each structural element. Consequently, it is possible to appropriately modify the hardware configuration to be used according to the technological level at the time of carrying out the present embodiment.

It is possible to create a computer program used to implement each function of the system 900 as described above and to install the computer program in PC or the like. It is also possible to provide a computer readable recording medium that stores such computer program therein. An example of the recording medium includes a magnetic disk, an optical disk, a magneto-optical disk, and flash memory. The computer program described above may be delivered via a network without use of the recording medium.

5. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

The effects described in the specification are just explanatory or exemplary effects, and are not limiting. That is, the technology according to the present disclosure can exhibit other effects that are apparent to a person skilled in the art from the descriptions in the specification, along with the above effects or instead of the above effects.

For example, in the foregoing embodiments, the acting forces on the forceps 110 are calculated, but the present technology is not limited to such an example. With the present technology, the target for which acting forces are calculated is not limited to the forceps 110, and it is possible to calculate the acting forces on any other type of rod-shaped member. For example, the target for which acting forces are calculated may be another surgical tool other than the forceps 110. Also, such a rod-shaped member is not limited to a surgical tool used in the medical field. The present technology is also applicable to various rod-shaped members in other technical fields.

Additionally, the present technology may also be configured as below.

(1)

An information processing device, including:

an acting force calculation unit that calculates, on a basis of a first detected value by a first force sensor provided on one side of a rod-shaped member, at least one of acting forces on a first point of action and a second point of action that differ from each other on an other side of the rod-shaped member.

(2)

The information processing device according to (1), wherein the acting force calculation unit calculates the acting force based on an equilibrium formula of the first detected value, the acting force on the first point of action, and the acting force on the second point of action.

(3)

The information processing device according to (2), wherein the acting force calculation unit calculates the acting force by simplifying the equilibrium formula based on a constraint condition corresponding to a usage mode of the rod-shaped member.

(4)

The information processing device according to any one of (1) to (3), wherein the first force sensor is a six-axis force sensor that detects forces in three mutually orthogonal axis directions, and moments about the three axis.

(5)

The information processing device according to any one of (1) to (4), wherein the first point of action is a leading edge on the other side of the rod-shaped member.

(6)

The information processing device according to any one of (1) to (5), wherein the rod-shaped member is forceps that are inserted into a body cavity of a patient during an endoscopic surgery.

(7)

The information processing device according to (6), wherein the second point of action is a site of contact between an inner wall of a trocar and the forceps when the trocar and the forceps are inserted into an opening made in a body of the patient, the site of contact being at a position where an outer wall of the trocar contacts a perimeter of the opening.

(8)

The information processing device according to any one of (1) to (7), further including:

a second force sensor that detects a torque of a drive shaft of a motor that drives the rod-shaped member, wherein the acting force calculation unit calculates the acting force by removing an influence of a driving force of the motor, based on a second detected value by the second force sensor.

(9)

The information processing device according to (8), further including:

an active acting force removal unit that calculates a force and a moment applied to the rod-shaped member according to the driving force of the motor, based on the second detected value, and subtracts the calculated force and moment from the first detected value, wherein the acting force calculation unit calculates the acting force based on the first detected value from which is subtracted the force and moment applied to the rod-shaped member according to the driving force of the motor.

(10)

The information processing device according to any one of (1) to (9), wherein the rod-shaped member is attached to an arm unit of a support arm device of a master-slave type which is remotely operated by an operator via a controller, and a control device of the support arm device feeds back the acting force on the first point of action calculated by the acting force calculation unit to the operator via the controller.

(11)

The information processing device according to any one of (1) to (10), wherein the rod-shaped member is attached to an arm unit of a support arm device, and a control device of the support arm device controls driving of the arm unit based on the acting force on the first point of action calculated by the acting force calculation unit.

(12)

The information processing device according to (11), wherein the acting force calculation unit calculates the acting force by removing an influence of a weight of the rod-shaped member itself, based on information about a position and an orientation of the arm unit and the rod-shaped member stored by the control device.

(13)

The information processing device according to (12), wherein the acting force calculation unit removes the influence of the weight of the rod-shaped member itself by calculating a force and a moment applied to the rod-shaped member according to the weight of the rod-shaped member itself, and subtracting the calculated force and moment from the first detected value.

(14)

The information processing device according to any one of (1) to (13), wherein a length of the rod-shaped member is variable, and the acting force calculation unit calculates the acting force according to a variation in the length of the rod-shaped member by recalculating an equilibrium formula of the first detected value, the acting force on the first point of action, and the acting force on the second point of action.

(15)

The information processing device according to any one of (1) to (14), wherein the rod-shaped member includes at least one joint section, and is configured so that a position and an orientation thereof are variable by the at least one joint section, and the acting force calculation unit calculates the acting force according to a variation in the position and the orientation of the rod-shaped member due to the joint section by recalculating an equilibrium formula of the first detected value, the acting force on the first point of action, and the acting force on the second point of action.

(16)

An information processing method, including:

calculating, by a processor, on a basis of a first detected value by a first force sensor provided on one side of a rod-shaped member, at least one of acting forces on a first point of action and a second point of action that differ from each other on an other side of the rod-shaped member.

(17)

A program causing a processor of a computer to realize:

a function of calculating, on a basis of a first detected value by a first force sensor provided on one side of a rod-shaped member, at least one of acting forces on a first point of action and a second point of action that differ from each other on an other side of the rod-shaped member.

REFERENCE SIGNS LIST 1, 2, 3, 4 system
110 forceps
120 motor
130 transmission member
131, 132 gear
133 wire
140 trocar
150 force sensor (first force sensor)
160 arm unit
170, 290 information processing device
171, 291 storage unit
172, 292 control unit
173, 294 acting force calculation unit
280 second force sensor
293 active acting force removal unit

The invention claimed is:

1. An information processing device, comprising:
processing circuitry configured to
receive a first detected value from a first force sensor, the first detected value corresponding to a plurality of forces detected by the first force sensor including a first force from a first point of action, a second force from a second point of action on a rod-shaped member, and a third force corresponding to a gravitational force,
receive a second detected value from a second force sensor, the second detected value corresponding to a torque force detected by the second force sensor, the torque force including forces applied by a driving force of a motor, subtract a portion of the torque force from the first detected value based on the second detected value, calculate acting forces on one or more of the first point of action and the second point of action based on a value obtained by the subtracting of the portion of the torque force from the first detected value, and control the motor based on the calculated acting forces.

2. The information processing device according to claim 1, wherein the acting force is calculated based on an equilibrium formula of the first detected value, the acting force on the first point of action, and the acting force on the second point of action.

3. The information processing device according to claim 2, wherein the acting force is calculated by simplifying the equilibrium formula based on a constraint condition corresponding to a usage mode of the rod-shaped member.

4. The information processing device according to claim wherein the first force sensor is a six-axis force sensor that detects forces in three mutually orthogonal axis directions and moments about the three axes.

5. The information processing device according to claim 1, wherein the first point of action is a leading edge on of the rod-shaped member.

6. The information processing device according to claim 1, wherein the rod-shaped member is forceps that are inserted into a body cavity of a patient during an endoscopic surgery.

7. The information processing device according to claim 6, wherein the second point of action is a site of contact between an inner wall of a trocar and the forceps when the trocar and the forceps are inserted into an opening made in a body of the patient, the site of contact being at a position where an outer wall of the trocar contacts a perimeter of the opening.

8. The information processing device according to claim 1, wherein the rod-shaped member is attached to an arm unit of a support arm device of a master-slave type which is remotely operated by an operator via a controller, and a control device of the support arm device feeds back the acting force on the first point of action to the operator via the controller.

9. The information processing device according to claim 1, wherein the rod-shaped member is attached to an arm unit of a support arm device, and a control device of the support arm device controls driving of the arm unit based on the acting force on the first point of action.

10. The information processing device according to claim 9, wherein the processing circuitry is further configured to calculate the acting force by removing an influence of a weight of the rod-shaped member itself, based on information about a position and an orientation of the arm unit and the rod-shaped member stored by the control device.

11. The information processing device according to claim 10, wherein the processing circuitry is further configured to remove the influence of the weight of the rod-shaped member itself by calculating a force and a moment applied to the rod-shaped member according to the weight of the rod-shaped member itself, and subtracting the calculated force and moment from the first detected value.

12. The information processing device according to claim 1, wherein a length of the rod-shaped member is variable, and the processing circuitry is further configured to calculate the acting force according to a variation in the length of the rod-shaped member by recalculating an equilibrium formula of the first detected value, the acting force on the first point of action, and the acting force on the second point of action.

13. The information processing device according to claim 1, wherein the rod-shaped member includes at least one joint section, and is configured so that a position and an orientation of the rod-shaped member are variable by the at least one joint section, and the processing circuitry is further configured to calculate the acting force according to a variation in the position and the orientation of the rod-shaped member due to the joint section by recalculating an equilibrium formula of the first detected value, the acting force on the first point of action, and the acting force on the second point of action.

14. An information processing method, comprising:

receiving, by processing circuitry, a first detected value from a first force sensor, the first detected value corresponding to a plurality of forces detected by the first force sensor including a first force from a first point of action, a second force from a second point of action on a rod-shaped member, and a third force corresponding to a gravitational force;

receiving, by the processing circuitry, a second detected value from a second force sensor, the second detected value corresponding to a torque force detected by the second force sensor, the torque force including forces applied by a driving force of a motor;

subtracting, by the processing circuitry, a portion of the torque force from the first detected value based on the second detected value;

calculating, by the processing circuitry, acting forces on one or more of the first point of action and the second point of action based on a value obtained by the subtracting of the portion of the torque force from the first detected value; and controlling, by the processing circuitry, the motor based on the calculated acting forces.

15. A non-transitory computer-readable storage medium storing computer-readable instructions thereon which, when executed by a computer, cause the computer to perform a method, the method comprising:

receiving a first detected value from a first force sensor, the first detected value corresponding to a plurality of forces detected by the first force sensor including a first force from a first point of action, a second force from a second point of action on a rod-shaped member, and a third force corresponding to a gravitational force;

receiving a second detected value from a second force sensor, the second detected value corresponding to a torque force detected by the second force sensor, the torque force including forces applied by a driving force of a motor;

subtracting a portion of the torque force from the first detected value based on the second detected value;

calculating acting forces on one or more of the first point of action and the second point of action based on a value obtained by the subtracting of the portion of the torque force from the first detected value; and controlling the motor based on the calculated acting forces.

* * * * *